(12) United States Patent
Kulkarni et al.

(10) Patent No.: US 9,044,607 B2
(45) Date of Patent: Jun. 2, 2015

(54) SPECTRAL CONTRAST ENHANCEMENT IN A COCHLEAR IMPLANT SPEECH PROCESSOR

(71) Applicant: Advanced Bionics AG, Staefa (CH)

(72) Inventors: Abhijit Kulkarni, Newbury Park, CA (US); Leonid M. Litvak, Los Angeles, CA (US); Aniket Saoji, Ann Arbor, MI (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/079,326

(22) Filed: Nov. 13, 2013

(65) Prior Publication Data

US 2014/0074183 A1    Mar. 13, 2014

Related U.S. Application Data

(63) Continuation of application No. 12/175,151, filed on Jul. 17, 2008, now Pat. No. 8,600,516.

(60) Provisional application No. 60/950,324, filed on Jul. 17, 2007.

(51) Int. Cl.
*A61N 1/36* (2006.01)
*G10L 19/02* (2013.01)

(52) U.S. Cl.
CPC ........ *A61N 1/36032* (2013.01); *G10L 19/0212* (2013.01)

(58) Field of Classification Search
CPC .................. A61N 1/36032; A61N 2005/0605; A61N 2005/0626; A61N 1/05; A61B 5/7225; A61B 5/726; A61B 5/121; A61B 5/7257; A61B 5/686; A61F 11/00; H04R 2225/43; H04R 25/505; G10L 21/0232; G10L 25/48
USPC ...................... 607/1–2, 55–57, 115–116, 118
See application file for complete search history.

(56) References Cited

U.S. PATENT DOCUMENTS 7,242,985 B1    7/2007    Fridman et al.
8,694,114 B2 *  4/2014    Churchill ........................ 607/57

FOREIGN PATENT DOCUMENTS

WO    02/17678 A1    2/2002

OTHER PUBLICATIONS

Baer, Thomas, PhD, et al., Spectral contrast enchancement of speech in noise for listeners with sensorineural hearing impairment: effects on intelligibility, quality, and response times; Journal of Rehabilitation Research and Devleopment; (1993); pp. 49-72; vol. 30 No. 1.
Arifianto, Dhany; Dual Parameters for Voiced-Unvoiced Speech Signal Determination; IEEE; (2007); pp. 749-752.

(Continued)

*Primary Examiner* — Deborah Malamud
(74) *Attorney, Agent, or Firm* — Wong, Cabello, Lutsch, Rutherford & Brucculeri, L.L.P.

(57) ABSTRACT

Among other things, enhancing spectral contrast for a cochlear implant listener includes detecting a time domain signal. A first transformation is applied to the detected time domain signal to convert the time domain signal to a frequency domain signal. A second transformation is applied to the frequency domain signal to express the frequency domain signal as a sum of two or more components. A sensitivity of the cochlear implant listener to detect modulation of each component is obtained.

9 Claims, 17 Drawing Sheets

(56) References Cited

OTHER PUBLICATIONS

Hayes, Don, PhD; Speech Enchancement: Surprising Benefits for Soft and Distant Speech; Unitron Hearing-Element™; pp. 2-8.

Abe, Toshihiko et al., Robust Pitch Estimation with Harmonics Enhancement in Noisy Enviroments Based on Instantaneous Frequency; Precision and Intelligent Laboratory Tokyo Institute of Technology, Yokohama, Japan.

Ellis, Dan; Lecture 8: Pitch Tracking; Elen E4896 Music Signal Processing; Dept. Electrical Engineering, Columbia University.

Hasan, Kamrul MD. et al., Signal reshaping using dominant harmonic for pitch estimation of noisy speech; Signal Processing; (2006); pp. 1010-1018; 86.

Nehorai, Arye et al., Adaptive Comb Filtering for Harmonic Signal Enchancement; IEEE Transactions on Acoustics, Speech, and Signal Processing, (Oct. 1986); pp. 112-1138; vol., ASSP-34.

Clarkson, Peter M. et al.; Envelope expansion methods for speech enchancement; J. Accoust.Soc. Am; (Mar. 1991);pp. 1378-1382; vol. 89, No. 3.

Wikipedia, the free encyclopedia; "Wavelet," downloaded from World Wide Web at http://en.wikipedia.org/wiki/Wavelet on Jul. 13, 2008.

\* cited by examiner

SPECTRAL CONTRAST ENHANCEMENT IN A COCHLEAR IMPLANT SPEECH PROCESSOR

CROSS-REFERENCES TO RELATED APPLICATIONS

This application is a continuation of U.S. patent application Ser. No. 12/175,151, filed Jul. 17, 2008, now U.S. Pat. No. 8,600,516, which is a Non-Provisional of U.S. patent application Ser. No. 60/950,324, filed Jul. 17, 2007. Priority is claimed to all of these applications, which are incorporated herein by reference in their entireties, including the Appendices of U.S. patent application Ser. No. 60/950,324.

TECHNICAL FIELD

The following disclosure relates to implantable neurostimulator devices and systems, for example, cochlear stimulation systems, and to sound processing strategies employed in conjunction with such systems.

BACKGROUND

At least partial hearing may be restored to the profoundly deaf by using various techniques for delivering electrical stimuli to the auditory nerve. The auditory sensations elicited by such electrical stimulation may be perceived by the profoundly deaf as sounding similar to normal speech. The electrical stimulation can be implemented through a prosthetic device, known as a cochlear implant (CI), which is implanted in the inner ear. Cochlear implants can employ an electrode array that is inserted into the cochlear duct. One or more electrodes of the array can selectively stimulate different auditory nerves at different places in the cochlea based on the pitch of a received sound signal.

SUMMARY

The methods, systems and computer program products described in this specification implement techniques for clarifying sound as perceived through a cochlear implant. In particular, the methods, systems and computer program product described in this specification implement techniques for customizing a speech processing strategy in conjunction with psychophysical tests to provide optimal spectral enhancements of contrasts between stimulation signals as perceived through an individual cochlear implant.

In one aspect, providing spectral contrast enhancement for a cochlear implant listener includes detecting a time domain signal. A first transformation is applied to the detected time domain signal to convert the time domain signal to a frequency domain signal. Also, a second transformation is applied to the frequency domain signal to express the frequency domain signal as a sum of two or more components. A sensitivity of a cochlear implant listener to detect modulation of each component is obtained.

Implementations can optionally include one or more of the following features. Based on the obtained sensitivity of the cochlear implant listener, contribution of select one or more of the components can be enhanced during signal reconstruction. Enhancing the contribution can include enhancing the contribution of select one or more of the components during signal reconstruction that uses lateral suppression. Also, applying the first transformation can include applying a linear transformation. Further, applying the linear transformation can include applying either a Fourier transformation or a wavelet transformation. Also, applying the second transformation can include applying a linear transformation. Again, applying this linear transformation as the second transformation can include applying either a Fourier transformation or a wavelet transformation.

In another aspect, providing spectral contrast enhancement includes detecting a time domain signal, and transforming the detected time domain signal to obtain a frequency domain signal spectrum. Based on a spatial selectivity of a cochlear implant listener, a frequency dependent enhancement is applied to the obtained signal spectrum. Implementations can optionally include one or more of the following features. Applying the frequency dependent enhancement can include raising the signal spectrum to a power factor that is great than one. In addition a signal quality of the signal spectrum at each frequency can be detected. Also, applying the frequency dependent enhancement can include applying an enhancement at each frequency with acceptable signal quality. Further, a power factor that is less than one can be applied when detected that the signal quality of the signal spectrum indicates undesired noise.

In another aspect, a speech processing strategy can be adjusted by determining a spectral modulation transfer function of a cochlear implant user. Once the spectral modulation transfer function is determined, an enhancement filter function can be selected to match the determined spectral modulation transfer function. In addition, filter parameters of the enhancement filter function can be generated based on the spectral modulation transfer function. Then, a speech processing strategy can be adjusted based on the generated filter parameters.

Implementations may include one or more of the following features. For example, a psychophysical test can be administered to the cochlear implant user to determine the spectral modulation transfer function. The psychophysical test administered to the cochlear implant user can include a process of determining a smallest detectable spectral contrast as a function of a plurality of spectral modulation frequency bands. In addition, the enhancement filter function can be selected by comparing the spectral modulation transfer function of the cochlear implant user against a spectral modulation transfer function of a person with normal hearing and determining a ratio of the two spectral modulation transfer functions. The filter parameters can be generated by determining $\sigma$, $G_{max}$, and $G_{min}$, where $\sigma$ represents a width of the filter and $G_{max}$ and $G_{min}$ represents scaling and offset of the filter. Then, a speech processing strategy can be adjusted by adjusting an outer hair cell model based on the filter parameters. The outer hair cell model can be adjusted by determining a plurality of lateral suppression coefficients based on the filter parameters. Further, the filter parameters can be generated by fitting the enhancement filter function to the spectral modulation transfer function.

In another aspect, the techniques include enhancing a spectral contrast for a cochlear implant user by determining a spectral modulation transfer function for a cochlear implant user based on a smallest detectable spectral contrast for a plurality of spectral modulation frequencies. The determined spectral modulation transfer function of the cochlear implant user can be compared to a spectral modulation transfer function of a person having normal hearing. A ratio of the two spectral modulation transfer functions can also be determined to obtain an enhancement factor desired for the cochlear implant user. The techniques can also be implemented to generate filter parameters based on the spectral modulation transfer function and the enhancement factor. Further, the generated filter parameters can be used to adjust a speech processing strategy.

The techniques described in this specification can be implemented to realize one or more of the following advantages. For example, the techniques can be implemented to enhance the contrast between neighboring stimulation signals of a sound processing strategy and thus improve sound clarity and speech recognition, especially under difficult listening conditions. The techniques also can be implemented to provide tailored contrast enhancements for individual CI user. The techniques also can be implemented to decrease the power consumption of a cochlear implant system implementing a sound processing strategy. Further, the techniques can be implemented to reduce interaction between neighboring electrodes and the resulting influence on corresponding neurons by decreasing the stimulation level on one or more electrodes as a result of the stimulation level present on one or more neighboring electrodes.

These general and specific aspects can be implemented as apparatus, methods, systems, computer program products, or any combination of apparatus, methods, systems and computer program products.

BRIEF DESCRIPTION OF THE DRAWINGS

Like reference symbols indicate like elements throughout the specification and drawings.

DETAILED DESCRIPTION

Figure 1:
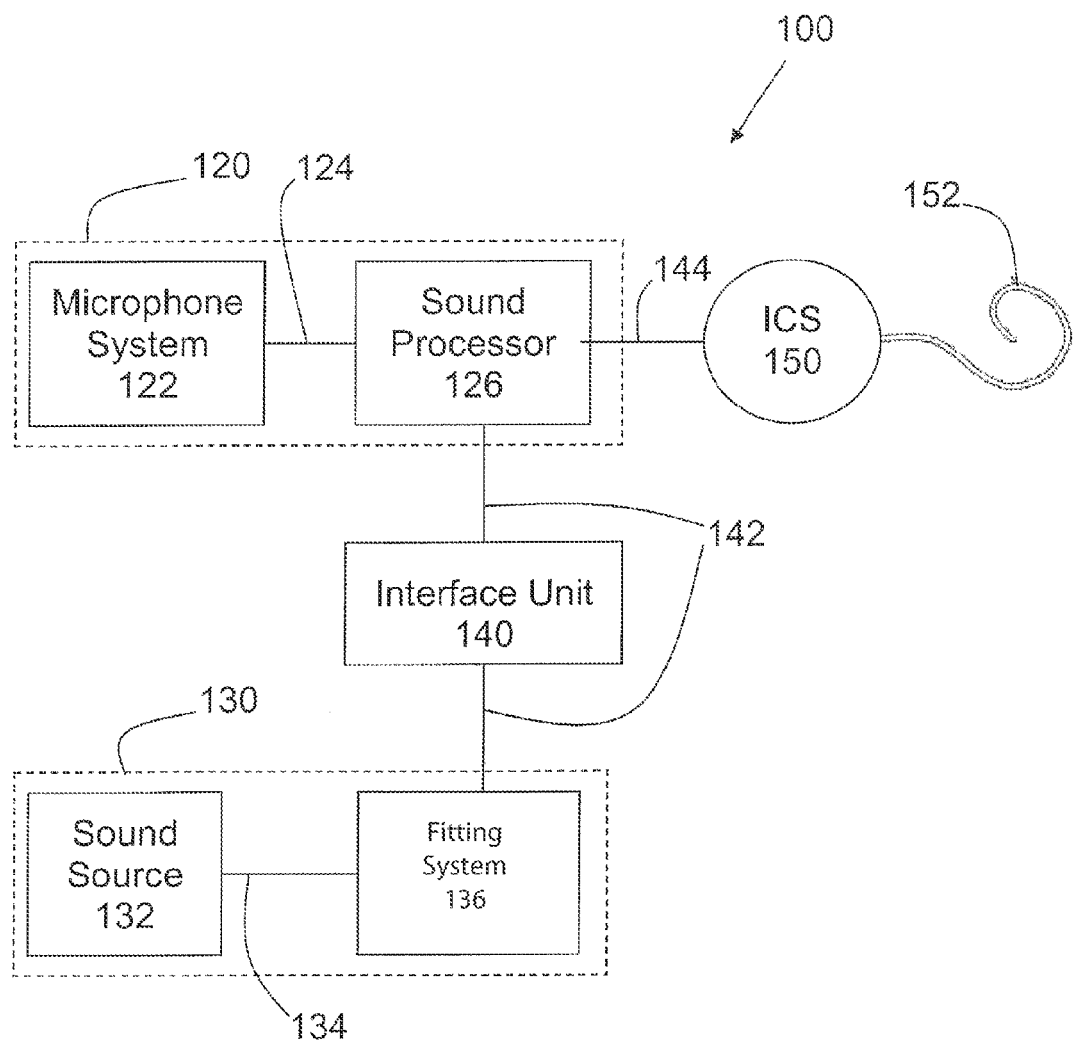
FIG. 1 is a block diagram of a spectral contrast enhancement system.

FIG. 1 represents a spectral contrast enhancement system 100 comprising a cochlear implant fitting portion 130 and a sound processor portion 120. The cochlear implant fitting portion 130 can include a fitting system 136 coupled to a sound source 132 through an appropriate communication link 134. The sound processor portion 120 can include a microphone system 122 coupled to a sound processor 126 through an appropriate communication link 124. The cochlear implant fitting portion 130 can generate an acoustic signal, which can be picked up and processed by the sound processor portion 120. The processed acoustic signal can be passed to an implantable cochlear stimulator (ICS) 150 through an appropriate communication link 144. The ICS 150 is coupled to an electrode array 152 configured to be inserted within the cochlea of a patient. The implantable cochlear stimulator 150 can apply the processed acoustic signal as a plurality of stimulating inputs to a plurality of electrodes distributed along the electrode array 152. The electrode array 152 may be substantially as shown and described in U.S. Pat. Nos. 4,819,647 and 6,129,753, both patents incorporated herein by reference. The sound processor portion 120 may be substantially as shown and described in U.S. Pat. No. 7,242,985 (the '985 patent), which is incorporated herein by reference in its entirety.

In some implementations, the cochlear implant fitting system 136, the sound source 132, the microphone system 122, and the sound processor 126 can be implemented as an external spectral contrast enhancement portion. The implantable cochlear stimulator 150 and the electrode array 152 can be an internal, or implanted portion. Thus, a communication link 144 coupling the sound processor 126 and the internal portion can be a transcutaneous (through the skin) link that allows power and control signals to be sent from the sound processor 126 to the implantable cochlear stimulator 150.

In other implementations, the implantable cochlear stimulator can send information, such as data and status signals, to the sound processor 126 over the communication link 144. To facilitate bidirectional communication between the sound processor 126 and the implantable cochlear stimulator 150, the communication link 144 can include more than one channel. Additionally, interference can be reduced by transmitting information on a first channel using an amplitude-modulated carrier and transmitting information on a second channel using a frequency-modulated carrier.

In an implementation whereby the implantable cochlear stimulator 150 and the electrode array 152 are implanted within the CI user, and the microphone system 122 and the sound processor 126 are carried externally (not implanted) by the CI user, the communication link 144 can be realized through use of an antenna coil in the implantable cochlear stimulator and an external antenna coil coupled to the sound processor 126. The external antenna coil can be positioned to be in alignment with the implantable cochlear stimulator, allowing the coils to be inductively coupled to each other and thereby permitting power and information, e.g., the stimulation signal, to be transmitted from the sound processor 126 to the implantable cochlear stimulator 150. In one implementation, the sound processor 126 and the implantable cochlear stimulator 150 can both be implanted within the CI user, and the communication link 144 can be a direct-wired connection or other suitable link as shown in U.S. Pat. No. 6,308,101, incorporated herein by reference.

The cochlear implant fitting portion 130 of the spectral contrast enhancement system 100 can be implemented to generate a known acoustic signal through the fitting system 136 and to output the acoustic signal through the sound source 132. The microphone system 122 senses the acoustic signal, whereby the acoustic signal can be converted to an electrical signal. The electrical signal can be sent to the sound processor 126 over an appropriate communication link 124, such as a circuit or bus. The sound processor 126 can be implemented to process the electrical signal in accordance with a sound processing strategy selected from various sound processing strategies, and thereby generate a control signal used to control the implantable cochlear stimulator. The control signal can specify or define the polarity, magnitude, location (which electrode pair or group is intended to receive the stimulation current), and timing (when the stimulation current is to be applied to the intended electrode pair or group) of the stimulation signal, such as a stimulation current generated by the implantable cochlear stimulator 150.

In general, magnitude and polarity of the stimulation current applied to the implanted electrodes of the electrode array can be adjusted in accordance with a specified sound processing strategy. The selected sound processing strategy can include defining a pattern of stimulation waveforms that are applied as controlled electrical currents to the electrodes of the electrode array implanted in a patient. Stimulation strategies can be implemented by modulating the amplitude of the stimulation signal or by modulating the frequency of the stimulation signal.

Figure 2:
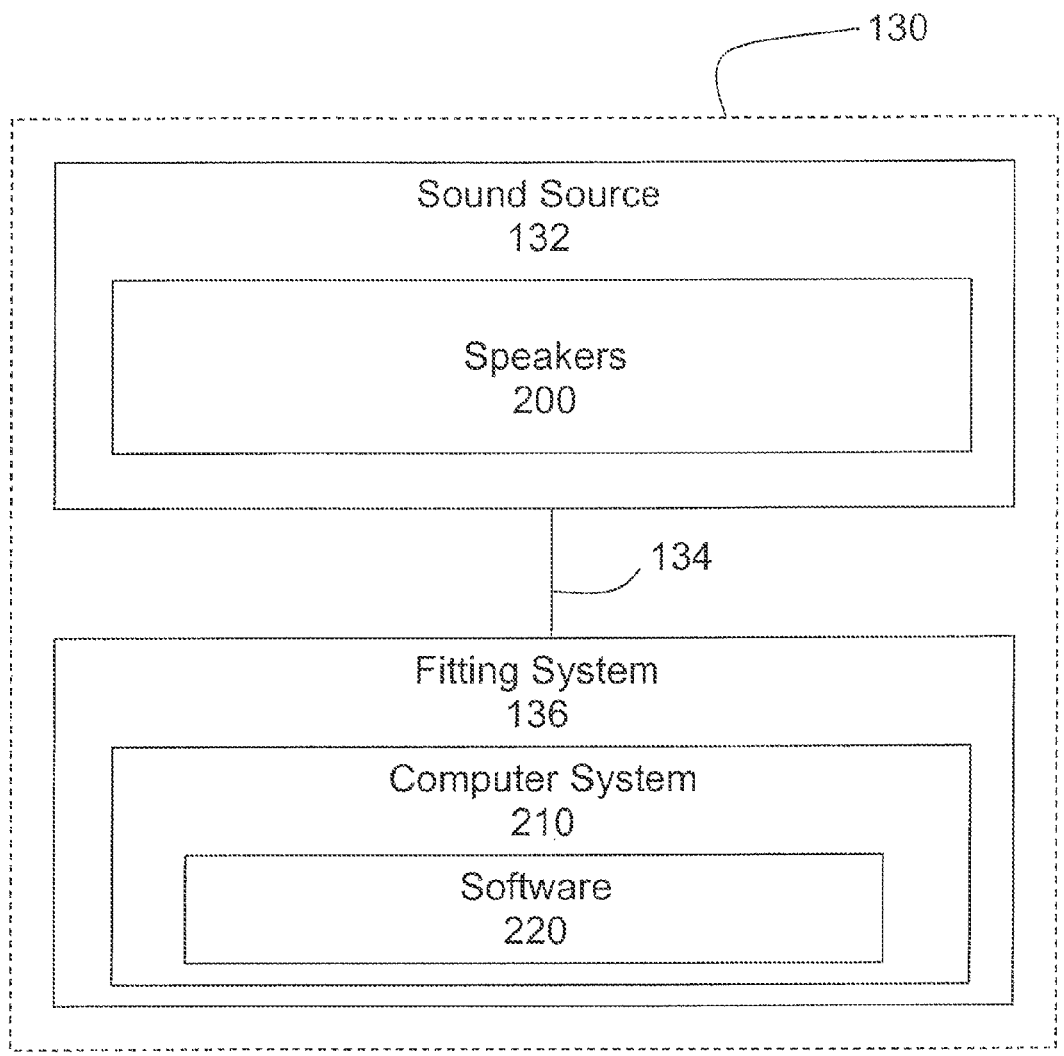
FIG. 2 is a block diagram of a cochlear implant fitting portion.

FIG. 2 represents a functional block diagram of the cochlear implant fitting portion 130. The CI fitting portion 130 facilitates "fitting" of the cochlear implant such that the parameters of the device being fitted are customized for the individual CI user. The CI fitting portion 130 may be substantially as shown and described in U.S. Pat. Nos. 5,626,629 and 6,289,247, both patents incorporated herein by reference. The fitting system 136 of the CI fitting portion 130 can be coupled to a sound source 132 comprising one or more speakers 200 or other suitable sound output devices. The fitting system 136 can further comprise a computer system 210 including a personal computer, portable computer, mobile device, equivalent device, or a combination thereof. Referring back to FIG. 1, the fitting system 136 can be coupled to the sound processor 126 through an interface unit (IU) 140, or an equivalent device. A communication link 142 can couple the IU 140 with the sound processor 126. In some implementations, the IU 140 may be included within the computer system 210 of the fitting system 136 as a built-in input/output (I/O) port or implemented as a detachable external device. The computer system 210, with or without the IU 140, can provide input signals to the sound processor 126 that can stimulate the acoustic signal sensed by the microphone system 122. Depending on the situation, the input signals generated by the computer system 210 of the fitting system 136 can replace the acoustic signal normally sensed by the microphone system 122 or provide command signals that supplement the acoustical signal sensed through the microphone system 122.

In some implementations, the computer system 210 of the fitting system 136 can include additional peripheral devices including a display device, a storage device, RAM, ROM, input/output (I/O) ports, a keyboard, a mouse, and other suitable peripheral devices. The computer system 120 can be configured to execute software 220 to control reading, displaying, delivering, receiving, assessing, evaluating and/or modifying both acoustic and electric stimulations sent to the sound processor 126. The software 220 can include computer programs such as firmware and other suitable computer executable instructions. The software 220 can facilitate generation of a known acoustic signal, which can be outputted through the sound source 132. The sound source 132 can comprise one or more speakers 200 placed in multiple locations. A display screen can be implemented to display, on a display device, a graphical user interface (GUI) executed as a part of the software 220 including selection screens, stimulation templates and other information generated by the software 220. The GUI can be implemented to facilitate an audiologist, other medical personnel, or even the CI user to easily view and modify all information necessary to control a fitting process.

In one implementation, the fitting system 136 can be implemented as a stand alone system located at the office of the audiologist or other medical personnel. A stand alone fitting system can allow the audiologist or other medical personnel to customize a sound processing strategy for the CI user during an initial fitting process after the implantation of the CI. The user can return to the office for subsequent adjustments as needed. The return visits may be required because the CI user may not be fully aware of his/her spectral contrast enhancement needs, and the user may become more perceptive of the sound quality provided by the sound processing strategy with the passage of time. The fitting system 136 can be implemented to include simple interfaces using hardware, software, or a combination of both hardware and software. For example, a simple set of hardware buttons, knobs, dials, slides, or similar interfaces can be implemented to select and adjust enhancement parameters. The interfaces can also be implemented as a GUI displayed on a screen.

In one implementation, the fitting system 136 can be implemented as a portable system. A portable fitting system can be provided to the CI user as an accessory device for allowing the CI user freedom to adjust the sound processing strategy as needed. The initial fitting process can be performed by the CI user aided by the audiologist or other medical personnel. After the initial fitting process, the user can perform subsequent adjustments without having to visit the audiologist or other medical personnel. The portable fitting system can be implemented to include simple user interfaces using hardware, software, or a combination of both hardware and software to facilitate the adjustment process as described above for the stand alone system implementation.

According to one feature of the techniques for clarifying sound as perceived through a cochlear implant, a fitting process can be implemented to determine a specific spectral contrast modulation strategy for the individual CI user. In one implementation, scaling factors applied to each envelope signals for the outer haircell model, which is described in detail in the '985 patent incorporated above, are determined based on spectral modulation threshold function (SMTF) for the individual CI user. The scaling factors thus determined are used to account for the interaction between frequency bands and thereby enhance the contrast between neighboring signals. Since the scaling factors determined are specifically tailored for each individual CI user, the effect of the outer haircell model can be optimized to accurately match the spectral enhancement needs for each individual CI user. Therefore the technique facilitates implementations of various flexible enhancement systems.

Often times, sensorineural impairments are not limited to auditory sensitivities, and thus requires more than just speech amplification. Listeners with sensorineural hearing loss also suffer from the inability to distinguish individual frequency components of spectrally complex stimuli. Frequency analysis in cochlear processing is analogous to a bank of overlapping band-pass filters, with each of the filters outputting a portion of the total spectrum of sound. In sensorineural impairments, mechanism for analyzing the sound spectrum into channels is altered due to auditory filters that are broader and abnormally asymmetrical. Processing through these abnormal filters may produce smearing of spectral details of the auditory stimuli that renders some portions of spectral contrasts undetectable. This is due to a reduction in the perceivable amplitude between peaks and valleys, which renders identification of specific frequency regions of energy concentration difficult to identify. Since frequency locations of spectral peaks are crucial cues to identity of speech sounds, spectral flattening may result in decreased speech perception ability.

In some implementations, to determine the scaling factors specific for each individual CI user, a psychophysical test is administered to the CI user using the CI fitting portion 136 whereby the smallest detectable spectral contrast can be determined for each spectral modulation frequency. For a given CI user, the SMTF describes the ability of the CI user to discriminate between a complex stimuli with an unmodulated or flat spectrum such as a white noise and one that has a sinusoidal ripple imposed on its spectrum. Each stimulus is composed of multiple tonal components spaced logarithmically across a frequency axis to ensure an equal number of tonal components in each ripple cycle across the stimulus bandwidth. Stimuli are generated with random starting phase values for each tonal components. The flat spectrum stimulus is generated with all tonal components having equal amplitude, and the ripple-spectrum stimuli contains variations in components amplitudes that are sinusoidal in log-log units, with ripple periods distributed over the logarithmic of frequency, and with the ripple amplitude described in decibels. Ripple frequency determines the spacing of peaks and valleys across the frequency range, and the amplitude of the ripple corresponds to the amount of spectral contrast present in the stimulus. Ripple frequencies are arranged in cycles per octave (CPO) and the ripple amplitude is varied during the test.

A CI user is seated in a sound-treated booth with a touchscreen for recording his responses to stimuli heard through a headphone. For each ripple frequency, the ripple amplitude is incrementally increased or decreased until a set percentage of correct discrimination is achieved. For each presentation to the CI user, multiple combination of stimuli are presented consecutively including one rippled spectrum of selected ripple frequency and one or more flat spectrum stimuli. When one flat spectrum stimulus and one rippled stimulus is presented, the CI user is asked to determine if the two stimuli are different. When two flat spectrum stimuli and one rippled stimulus are presented consecutively, the CI user is asked to select which stimulus is different from the other two stimuli. The ripple amplitude is initiated at a set dB (for example, 20 dB) peak-to-valley and increased by a small dB level (for example, 2 dB) after each incorrect response and decreased by a small dB level after each correct response. The dB step size is decreased (for example, to 0.5 dB) after a set number of reversal of directions (for example, four reversals) and the ripple amplitudes after a set number of reversals (for example ten reversals) are averaged. The average ripple amplitude represents the point at which the CI user is able to distinguish the rippled stimulus from the flat stimuli. This corresponds to a threshold value of the amplitude of modulation needed at a particular CPO. If the rippled stimulus is made very fast by increasing the number of cycles/octave, the CI user will need more spectral contrast to differentiate between the flat spectrum stimuli and the rippled stimuli. In general, the SMTF will show characteristics of lower modulation detection threshold at lower CPO and higher threshold at higher CPO. Therefore, the spectral contrast may need to be increased more at higher CPO than at lower CPO.

Figure 3:
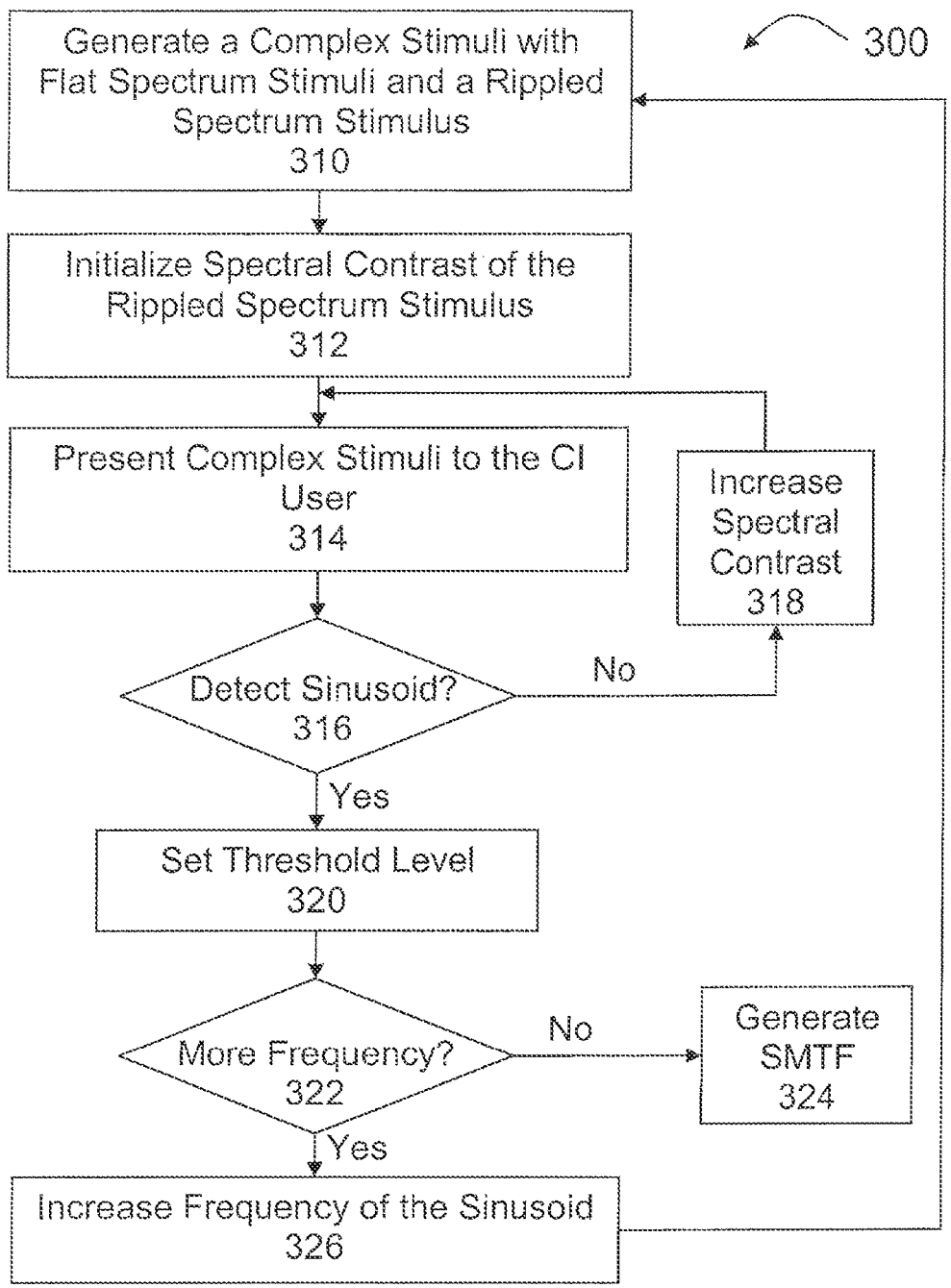
FIG. 3 is a flow chart describing a process of administering a SMTF psychophysical test to an individual cochlear implant user.

FIG. 3 describes a process of performing the psychophysical test 300 to determine the SMTF of the CI user. At 310, a complex stimuli including a flat spectrum stimulus and a rippled-spectrum stimulus is generated across a logarithmic frequency axis. The rippled spectrum stimulus is sinusoidal and can have a starting phase randomly selected from a range of 0 to $2\pi$. The rippled spectrum stimulus may be initialized, at 312, to a ripple amplitude corresponding to a spectral contrast too small for the CI user to distinguish the rippled spectrum stimulus from the flat spectrum stimuli. At 314, the sinusoidal rippled spectrum stimulus and one or more flat spectrum stimuli can be delivered to the CI user for detection. If the CI user is able to detect the difference between the sinusoidal rippled spectrum stimulus and the flat spectrum stimulus at 316, the amplitude level of the sinusoidal stimulus corresponding to the spectral contrast applied is noted as the threshold level for the frequency space (in CPO) at 320. If the CI user is not able to detect the sinusoidal rippled spectrum stimulus, the spectral contrast can be increased in small increments at 318 until a threshold level is reached, whereby the CI user is able to discriminate the sinusoidal rippled spectrum stimulus from flat spectrum stimuli. At 322, a determination is made if any more thresholds needs to be obtained for other spectral modulation frequencies. If threshold values have been determined at all the necessary spectral modulation frequencies, the SMTF is generated at 324 as a function of CPO. If threshold needs to be measured for additional spectral modulation frequencies, the number of cycles in the sinusoidal rippled spectrum stimulus are either increased or decreased as needed at 326. New complex stimuli are generated at 310, and 312 through 324 are repeated until a threshold level is determined for each available frequency band. The number of available frequency bands may correspond to the total number of electrodes implemented in the electrode array 152 of the internal or implanted portion.

Figure 4:
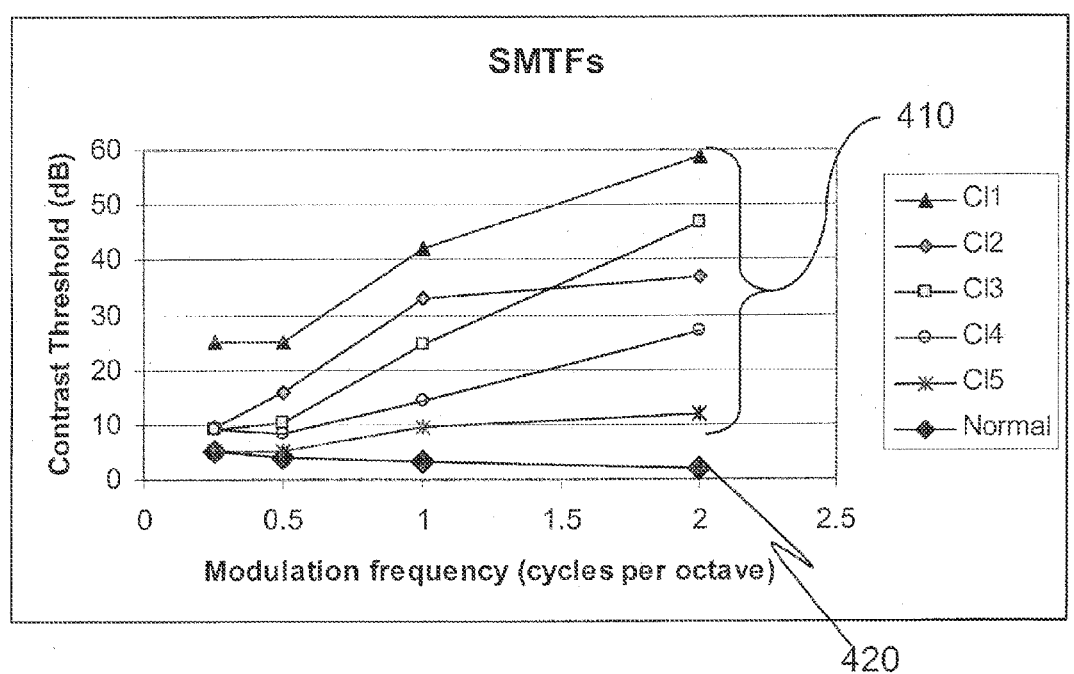
FIG. 4 represents a graph of SMTFs of cochlear implant users listening without any spectral contrast enhancement strategy.

FIG. 4 depicts a sample SMTF chart 400 illustrating SMTFs determined for multiple CI users listening through a non-enhanced sound processing strategy 410. In addition, the average SMTF for listeners with normal hearing 420 is also represented. The ratio between the SMTF of the CI user and a normal hearing listener provides the optimal amount of spectral enhancement for the CI user. Then, a sound processing strategy may be adjusted to provide the optimal spectral contrast enhancement for different modulation frequencies specifically tailored to the CI user.

Figure 5:
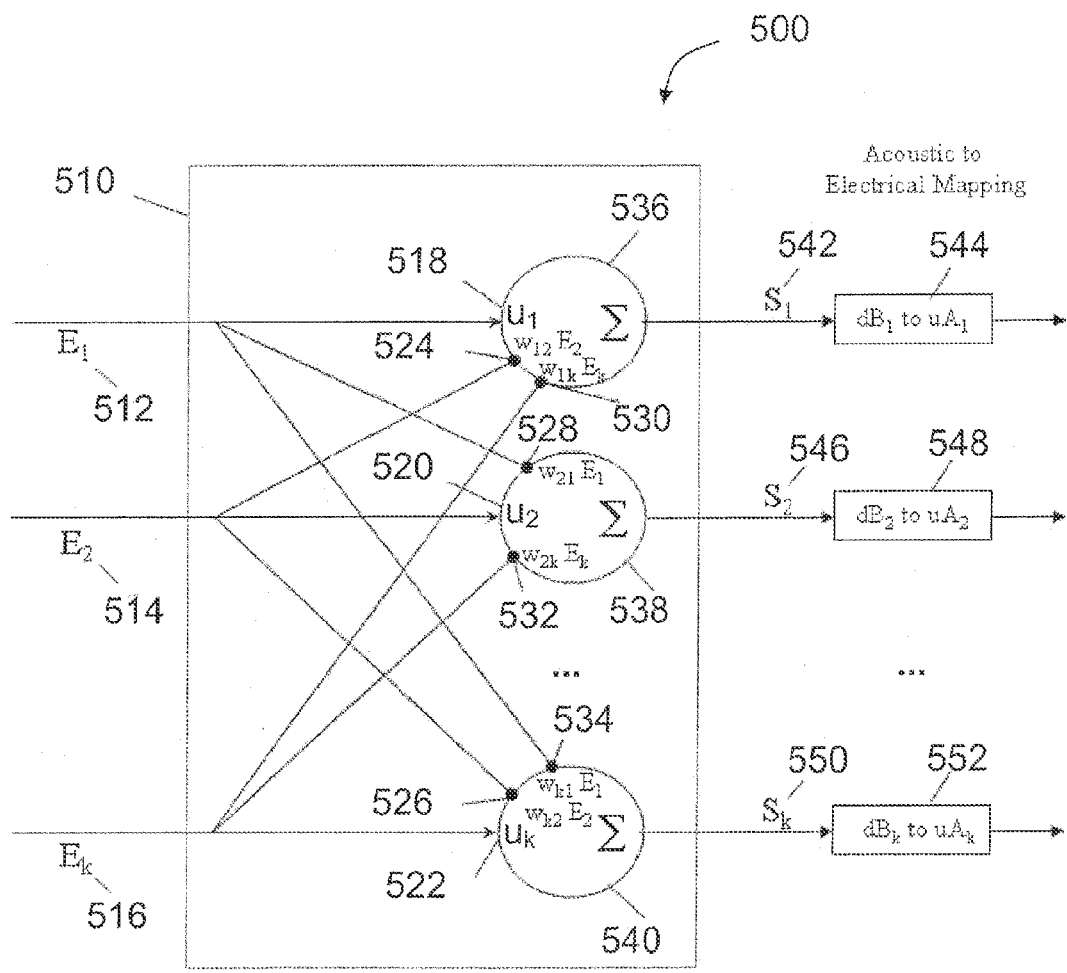
FIG. 5 is a functional block diagram of a lateral suppression network of a sound processing system.

FIG. 5 represents a functional diagram detailing an implementation of a lateral suppression network 510 as it relates to the system 500 of the outer hair cell model as described in the above-incorporated '985 patent. Lateral suppression is the term used to describe the psychophysical effect by which the loudness perceived from one tone is diminished to some extent by the presence of a neighboring tone. The suppressive effect is particularly evident when a loud tone closely neighbors a quieter tone. Thus, lateral suppression operates to enhance the contrast between tones. However, the lateral suppression algorithm must be implemented such that it does not generate abnormal results. If a flat spectrum is input to the lateral suppression network 510, a flat spectrum should also be output from the lateral suppression network 510. Further, the lateral suppression network must account for the frequency bands representing the highest and lowest frequencies of the audio signal (now shown), the edge frequency bands. In the system 500, for example, the first frequency band and the $k_{th}$ frequency band are the edge frequency bands. Because only one frequency band is immediately adjacent to each edge frequency band, each edge frequency band would be subjected to less suppression without additional compensation. Therefore, the lateral suppression network 510 must compensate by adjusting one or more factors, such as the weighting factor u associated with the edge frequency band or one or more of the scaling factors w employed by the lateral suppression processor associated with the edge frequency band.

The suppressed signals output from the lateral suppression network 510 are converted to electrical signals using the acoustic-to-electrical mapping associated with the corresponding frequency bands and provided as stimulation signals to one or more electrode pairs of a cochlear implant. For example, the envelope signals E1 512, E2 514, and Ek 516 output from the bank of envelope detectors (not shown) are input into the lateral suppression network 510. The lateral suppression network 510 then suppresses one or more of the envelope signals E1 512, E2 514, and Ek 516 in accordance with envelope signals associated with neighboring frequency bands, including the envelope signals E1 512, E2 514, and Ek 516. The lateral suppression network 510 then outputs the corresponding suppressed signals S1 542, S2 546, and Sk 550 respectively.

The suppressed signal $S_1$ 542 associated with the first frequency band is then converted into an electrical signal using the acoustic-to-electrical mapping 544 corresponding to the first frequency band. Similarly, the suppressed signal $S_2$ 546 associated with the second frequency band is then converted into an electrical signal using the acoustic-to-electrical mapping 548 corresponding to the second frequency band. Additionally, the suppressed signal $S_k$ 550 associated with the $k_{th}$ frequency band is then converted into an electrical signal using the acoustic-to-electrical mapping 552 corresponding to the $k_{th}$ frequency band.

In one implementation, the envelope signals $E_1$ 512, $E_2$ 514, and $E_k$ 516 are provided as inputs to the lateral suppression network 510. In the lateral suppression network 510, each envelope signal can be combined with one or more scaled envelope signals to account for the influence that envelope signals associated with neighboring frequency bands have on a particular envelope signal.

One or more of the envelope signals output from the bank of envelope detectors (not shown) can be weighted by a factor $u_i$ upon being provided to the lateral suppression network 510, where i represents the frequency band with which the envelope signal is associated. Thus, an envelope signal that is determined to be of greater importance than the envelope signals associated with neighboring frequency bands can be emphasized, such as an envelope signal representing an amplitude that exceeds a particular threshold value. Further, an envelope signal determined to be of lesser importance can be deemphasized, such as an envelope signal representing an amplitude that falls below a particular threshold value. In an implementation, each of the envelope signals provided to the lateral suppression network 510 can be weighted, and the weight associated with envelope signals that should not be emphasized or deemphasized can be set to 1.

For example, the envelope signals $E_1$ 512, $E_2$ 514, and $E_k$ 516 output from the bank of envelope detectors (not shown) are provided as inputs to the lateral suppression network 510. The lateral suppression processor 516 corresponding to the first frequency band multiplies the envelope signal $E_1$ 512 by a weighting factor $u_1$ 518 associated with the first frequency band. Similarly, the lateral suppression processor 538 corresponding to the second frequency band multiplies the envelope signal $E_2$ 514 by a weighting factor $u_2$ 520 associated with the second frequency band. The lateral suppression processor 540 corresponding to the $k_{th}$ frequency band multiplies the envelope signal $E_k$ 516 by a weighting factor $u_k$ 522 associated with the $k_{th}$ frequency band. As a result, the suppressive effect of signals associated with neighboring frequency bands will be diminished on envelope signals deemed to be of greater importance and increased on envelope signals deemed to be of lesser importance.

Because the influence that an envelope signal has on a neighboring envelope signal decreases as the number of frequency bands separating the envelope signals increases, the scaling factor applied to an envelope signal to generate a scaled envelope signal is selected as a function of the separation between the neighboring frequency bands. Therefore, a scaling factor $w_{ij}$ is chosen, where i represents the frequency band associated with the envelope signal being suppressed and j represents the frequency band associated with the envelope signal that is producing the suppressive effect. With each increase in the frequency band separation, the scaling factor $w_{ij}$ will further decrease the magnitude of the envelope signal being scaled. Additionally, as scaled envelope signals suppress an envelope signal, the scaling factor represents a negative value.

A laterally suppressed signal $S_i$ is generated by combining an envelope signal associated with a particular frequency band Ei with one or more scaled envelope signals wijEj associated with neighboring frequency bands. As discussed above, the envelope signal being suppressed also can be weighted using a weighting factor ui. The combining operation can be expressed mathematically as shown in Equation 1.

$$S_i = u_i E_i + \sum_{j \neq i} w_{ij} E_j \tag{Eq. 1}$$

Because nonlinearities are known to exist in the response of the basilar membrane, Equation 1 can be generalized as expressed in Equation 2, where $F_i(x)=X$ and $w_{ij}=0$. However, this simplification is not required and $S_i$ can be generated using a non-linear function in another implementation.

$$S_i = u_i E_i + F_i\left(\sum_j w_{ij} E_j\right) \tag{Eq. 2}$$

In an implementation, the envelope signal $E_1$ 512 associated with the first frequency band is provided to a corresponding lateral suppression processor 536. The lateral suppression processor 536 then multiplies the envelope signal $E_1$ 512 by the weighting factor $u_1$ 518. The lateral suppression processor 536 also receives as input the scaled envelope signal $w_{12}E_2$ 524, which represents the interaction of the envelope signal $E_2$ 514 associated with the second frequency band with the envelope signal $E_1$ 512 associated with the first frequency band. Additionally, the lateral suppression processor 536 receives as input the scaled envelope signal $w_{1k}E_k$ 530, which represents the interaction of the envelope signal $E_k$ 516 associated with the $k_{th}$ frequency band with the envelope signal $E_1$ 512 associated with the first frequency band. Further, the lateral suppression processor 536 can also receive as inputs the scaled envelope signals associated with any or all of the remaining third through $K-1_{th}$ frequency bands.

The lateral suppression processor 536 combines the envelope signal $E_1$ 512, weighted by $u_1$ 518, with at least the scaled envelope signals $w_{12}E_2$ 524 and $w_{1k}E_k$ 530, and outputs a laterally suppressed signal $S_1$ 542 associated with the first frequency band. The laterally suppressed signal $S_1$ 542 can then be converted to an electrical stimulation signal using the acoustic-to-electrical mapping 544 corresponding to the first frequency band.

A similar lateral suppression operation can be carried out for any or all of the envelope signals associated with the remaining frequency bands. For example, the lateral suppression processor 538 receives the envelope signal $E_2$ 514 associated with the second frequency band. The lateral suppression processor 538 then multiplies the envelope signal $E_2$ 514 by the weighting factor $u_2$ 520. The lateral suppression processor 538 also receives as inputs the scaled envelope signals $w_{21}E_1$ 528 and $w_{2k}E_k$ 532, which are associated with the first and $k_{th}$ frequency bands respectively. Additionally, the lateral suppression processor 538 can receive as inputs the scaled envelope signals associated with any or all of the remaining frequency bands. The lateral suppression processor 538 combines the envelope signal $E_2$ 514, weighted by $u_2$ 520, with the scaled envelope signals $w_{21}E_1$ 528 and $w_{2k}E_k$ 532, and outputs a laterally suppressed signal $S_2$ 546 associated with the second frequency band. The laterally suppressed signal $S_2$ 546 is then converted to an electrical stimulation signal using the acoustic-to-electrical mapping 548 associated with the second frequency band.

In an implementation, each lateral suppression processor of the lateral suppression network 510 can be configured to receive as inputs the scaled envelope signals associated with each of the neighboring frequency bands. Therefore, each of the envelope signals can be suppressed by scaled envelope signals associated with each of the neighboring frequency bands. If an envelope signal $E_b$ should not be used to suppress an envelope signal $E_a$, the scaling factor $w_{ab}$ can be set to 0.

Figure 6:
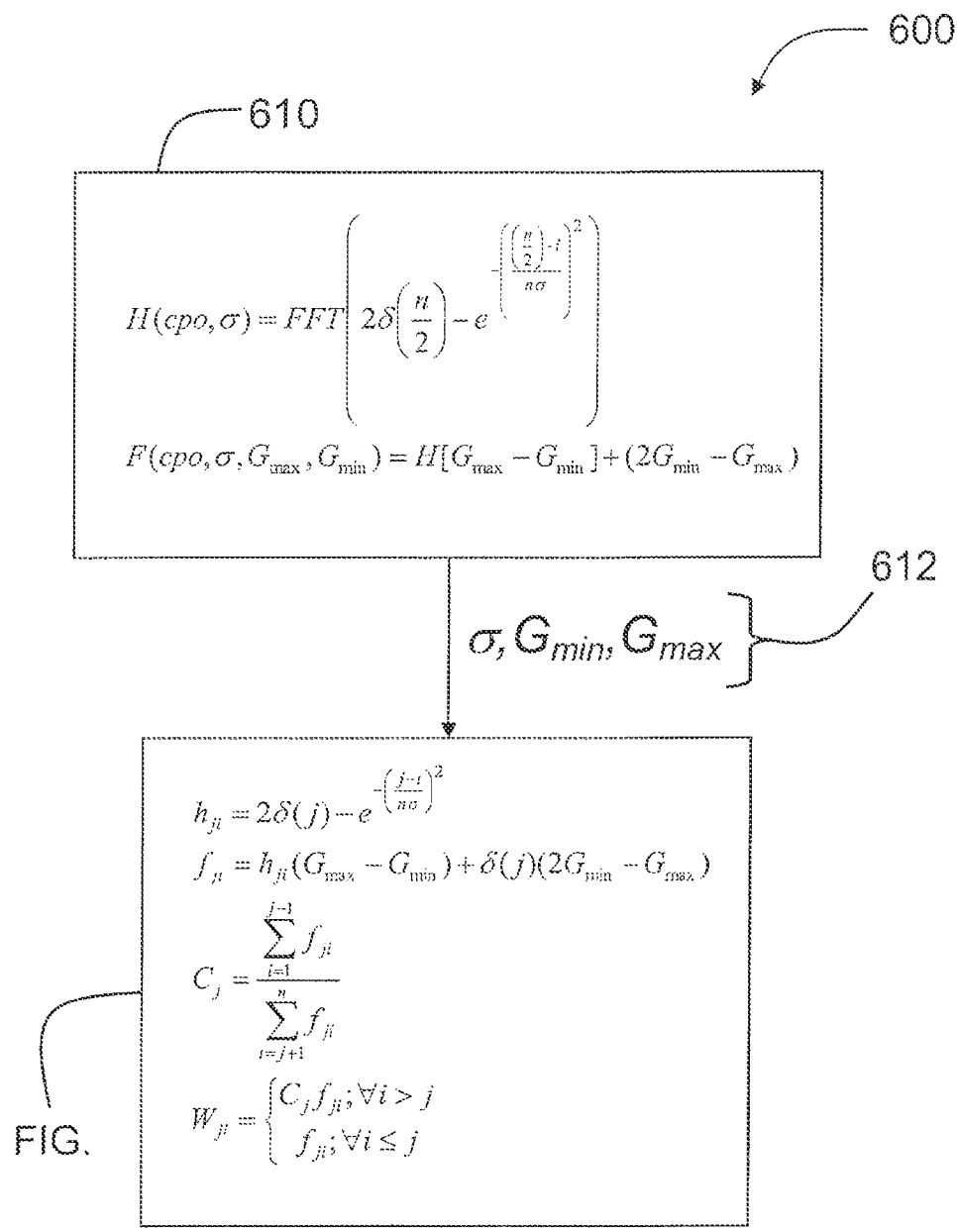
FIG. 6 describes a list of mathematical operations used to adjust a sound processing strategy based on the determined SMTF of the individual cochlear implant user.

FIG. 6 is a block diagram describing a process of adjusting a sound processing strategy 600 based on the outer haircell model as described in the above-incorporated '985 patent, which involves adjusting the "lateral suppression" coefficients. The adjustment process may be described in two steps. At 610, the SMTF determined for the CI user is analyzed to generate filter parameters 612 that best describes the SMTF. At 620, the filter parameters are applied in determining scaling factors for enhancement filters of the outer haircell model. Equations (3) and (4) describe functions used to determine the parameters based on SMTF of the CI user, and Equations (5), (6), (7), and (8) describe functions used to apply the filter parameters to determine the scaling factors of the enhancement filters in the outer haircell model. The equations are described more in detail below.

$$H(cpo, \sigma) = FFT\left(2\delta\left(\frac{n}{2}\right) - e^{-\left(\frac{(\frac{n}{2})-i}{n\sigma}\right)^2}\right) \quad \text{(Eq. 3)}$$

$$F(cpo, \sigma, G_{max}, G_{min}) = H[G_{max} - G_{min}] + (2G_{min} - G_{max}) \quad \text{(Eq. 4)}$$

$$h_{ji} = 2\delta(j) - e^{-\left(\frac{j-i}{n\sigma}\right)^2} \quad \text{(Eq. 5)}$$

$$f_{ji} = h_{ji}(G_{max} - G_{min}) + \delta(j)(2G_{min} - G_{max}) \quad \text{(Eq. 6)}$$

$$C_j = \frac{\sum_{i=1}^{j-1} f_{ji}}{\sum_{i=j+1}^{n} f_{ji}} \quad \text{(Eq. 7)}$$

$$W_{ji} = \begin{cases} C_j f_{ji}; & \forall i > j \\ f_{ji}; & \forall i \leq j \end{cases} \quad \text{(Eq. 8)}$$

Figure 7:
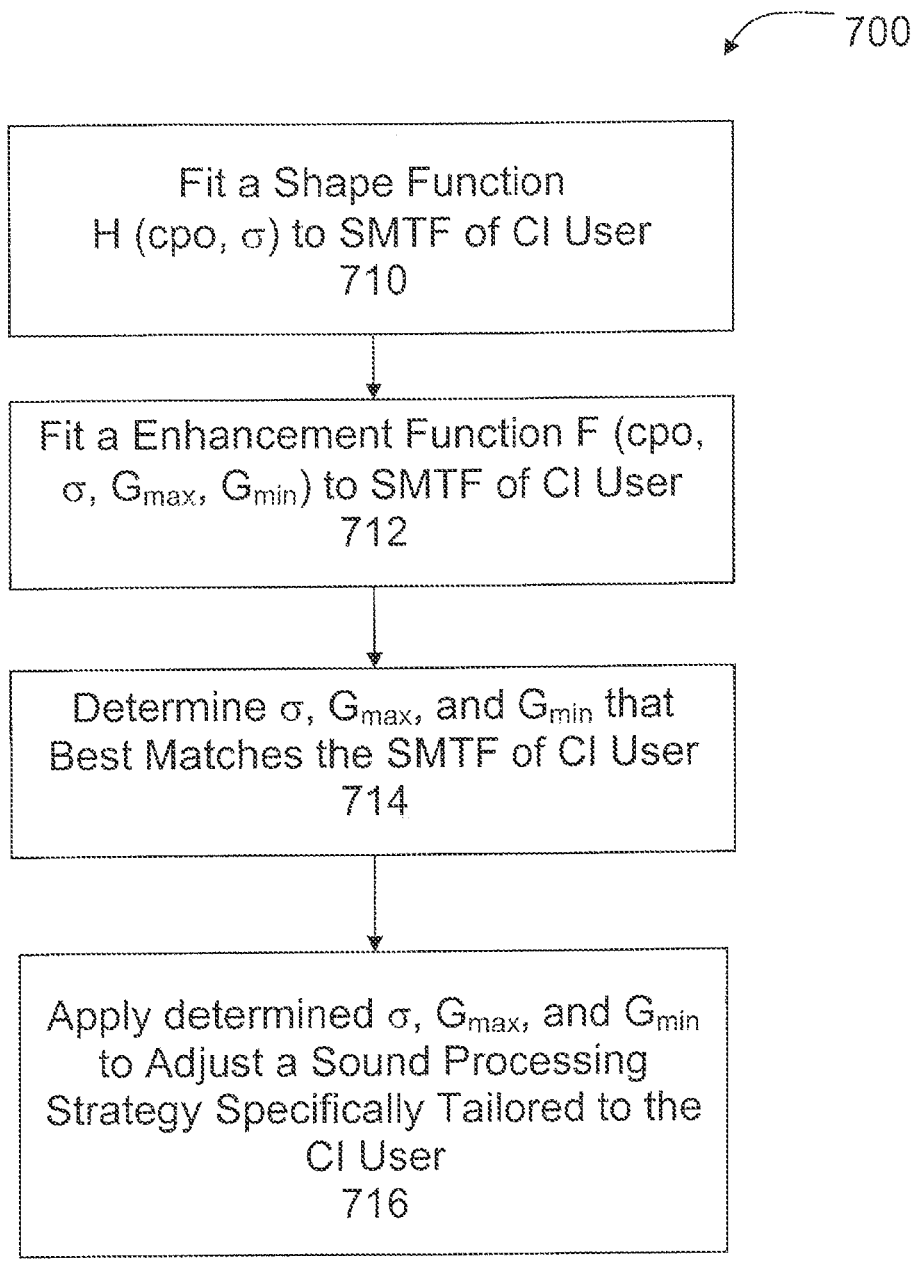
FIG. 7 is a flow chart describing a process of determining filter parameters based on the SMTF of the individual cochlear implant user.
Figure 8A:
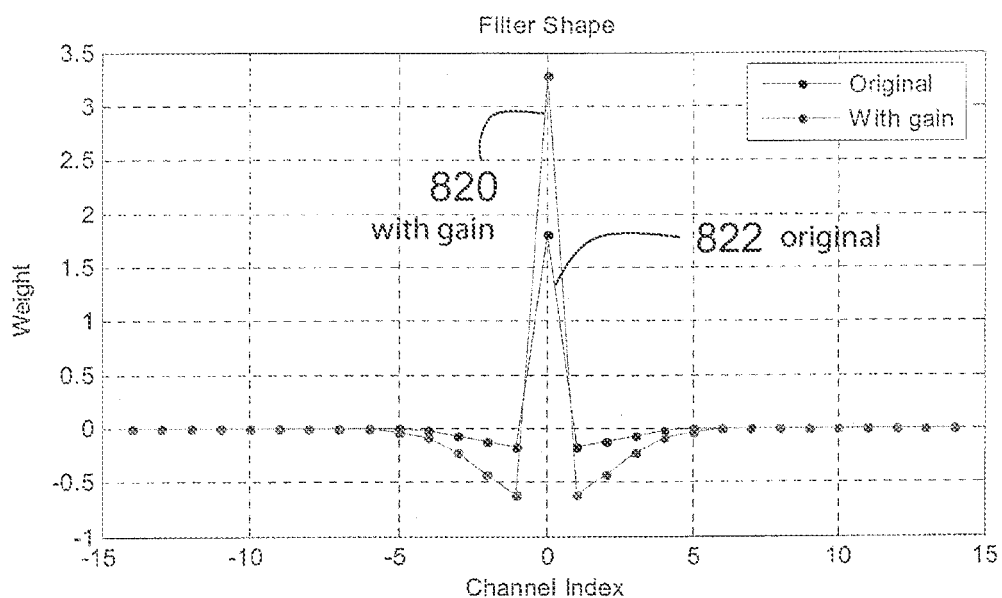
FIG. 8A is a graph illustrating the effect of filter parameters on the enhancement filter and scaling factor (weight).
Figure 8B:
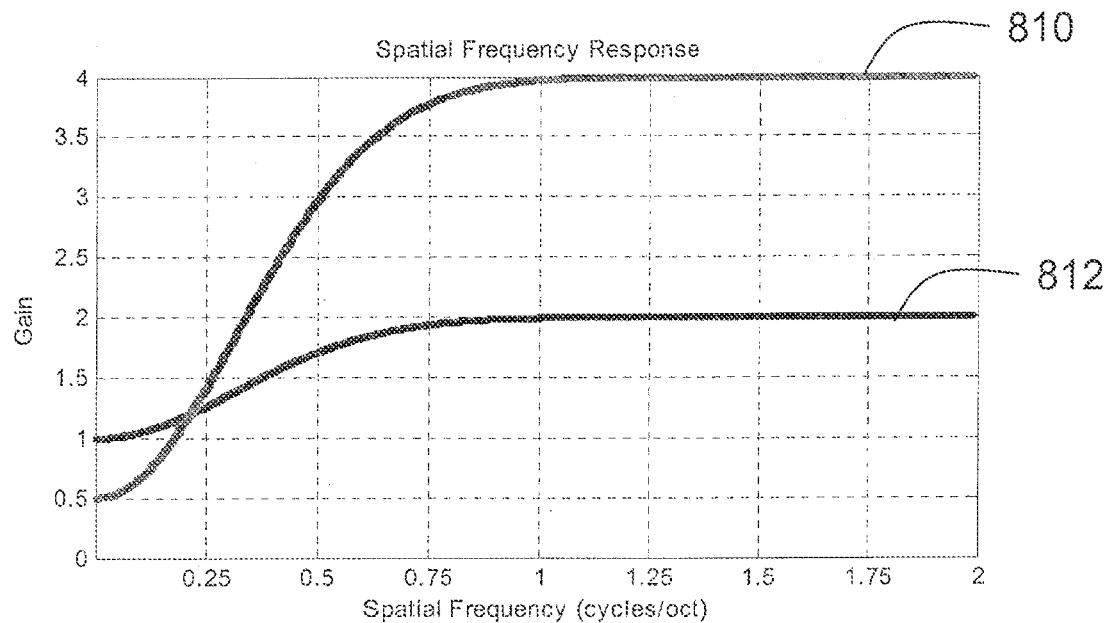
FIG. 8B is a graph illustrating the improvement in fitting a function to the SMTF by using $G_{max}$ and $G_{min}$ in comparison to a function using $\sigma$ alone
Figure 9:
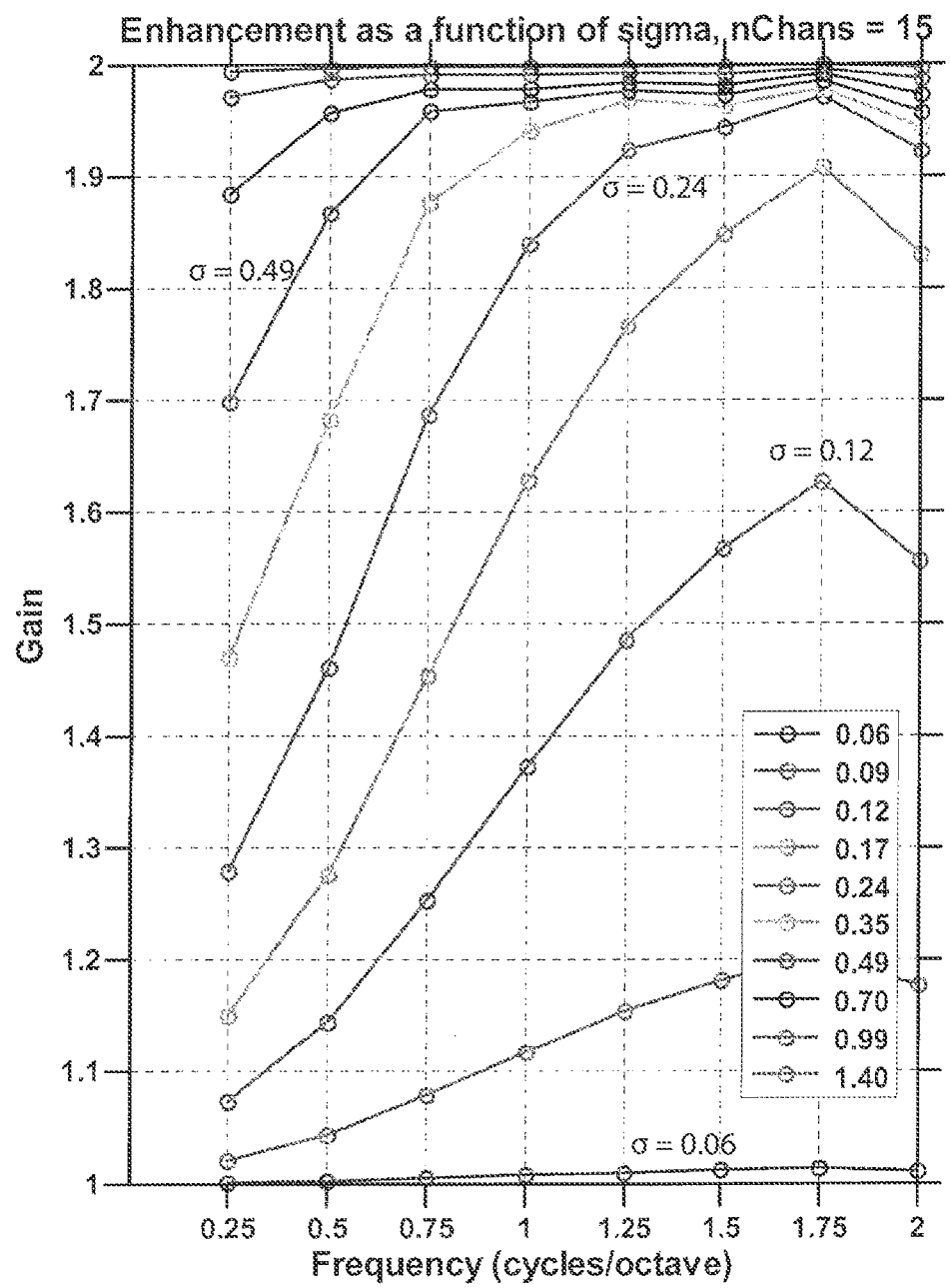
FIG. 9 is a graph listing various enhancement profiles plotted as a function of CPO by varying the value of $\sigma$.

FIG. 7 describes a process of determining the filter parameters corresponding to 610 above. A mathematical representation of threshold levels as a function of the available frequency band can be generated to define a spectral modulation transfer function (SMTF) of the CI user. The SMTF for the CI user is analyzed to generate at least three filter parameters, $\sigma$, $G_{max}$, and $G_{min}$. These filter parameters are generated by fitting a function to the SMTF of the CI user. At 710, a shape function, $H(CPO, \sigma)$, is generated and fit to the curve of the SMTF of the CI user to find the ideal $\sigma$ that best describes the shape of the curve. The shape function $H(CPO, \sigma)$ is a Fast Fourier Transform (FFT) of a generalized function for a central filter, $h_j$. At 712, the shape function is modified to incorporate scaling and offset to generate an enhancement function, $F(CPO, \sigma, G_{max}, G_{min})$, which is fit to the SMTF of the CI user to find the ideal $G_{max}$ and $G_{min}$ values to add scaling and offset in addition to the shape provided by $\sigma$. By incorporating the contribution of $G_{max}$ and $G_{min}$, the SMTF can be matched even better than possible with just $\sigma$. FIG. 8B depicts the improvement in the fit provided by the enhancement function, $F(CPO, \sigma, G_{max}, G_{min})$ (810) compared to the shape function, $H(CPO, \sigma)$ (812). At 714, $\sigma$, $G_{max}$, and $G_{min}$ are determined from the enhancement function. In addition, FIG. 9 illustrates a list of possible $F(CPO, \sigma, G_{max}, G_{min})$ that were fit to the SMTF of the CI user as a function of frequency. Each curve profile represents the effect of applying different $\sigma$ values to the function. Typically, the profile that best fits the optimal enhancement requirement of the individual CI user may be selected to determine the ideal $\sigma$. Appropriate sound processing strategy can be adjusted based on the determined $\sigma$, $G_{max}$, and $G_{min}$ to provide customized spectral enhancement strategy for the individual CI user at 716.

Figure 10:
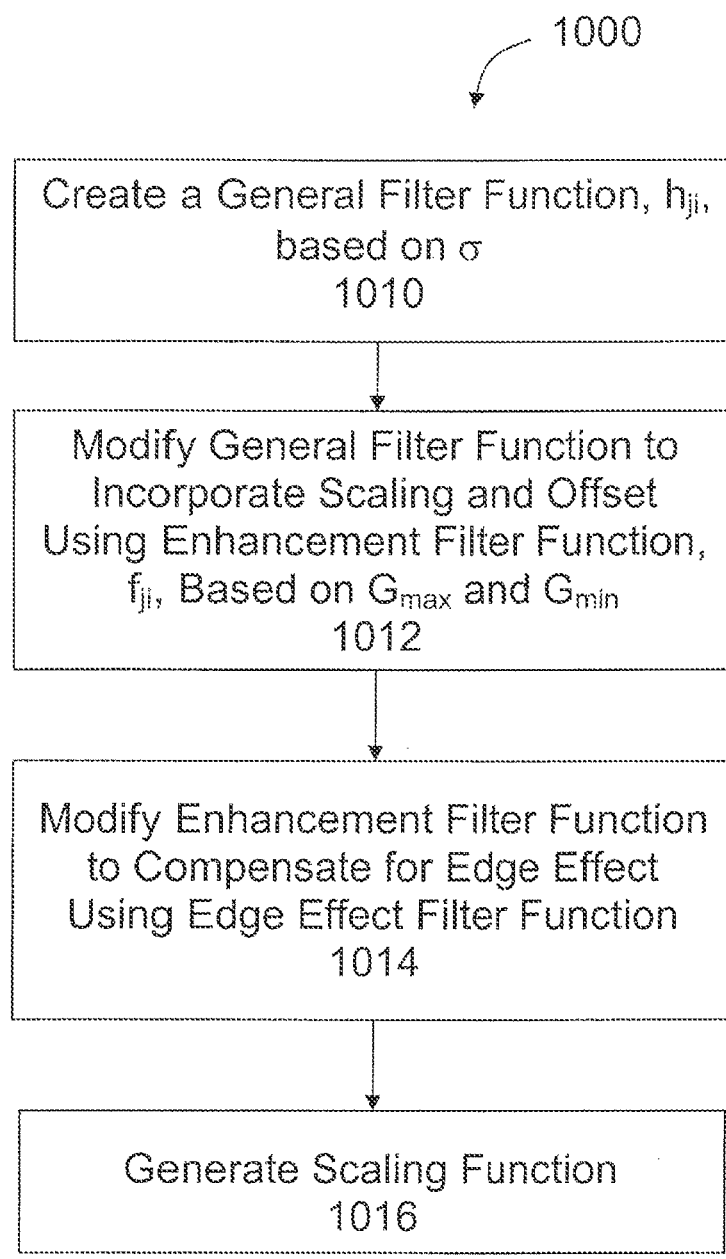
FIG. 10 is a flow chart describing a process of generating scaling factors based on the filter parameters $\sigma$, $G_{max}$, and $G_{min}$.

The filter parameters, $\sigma$, $G_{max}$, and $G_{min}$, can be used to determine the scaling factors, or the lateral suppression coefficients of the outer hair cell model customized for the individual CI user at 620 of FIG. 6 above. FIG. 10 depicts a process of determining the scaling factors applied to the outer haircell model. At 1010, a general filter function, $h_{ji}$, is generated based on the $\sigma$ determined for the CI user. Variable "j" represents the filter for which the enhancement is being calculated; variable "i" represents filter number; and constant "n" represents the number of channels corresponding to the number of electrodes implemented in the internal or implanted portion of the cochlear implant. A plot of function $h_{ji}$ 820 with respect to filter number, "i", is illustrated in FIG. 8A. The scaling factor for filter "j" is positive and the contributions from all other filters are subtracted to arrive at the gain enhancement shown. At 1012, the general filter function, $h_{ji}$, is modified by taking into account the contributions of $G_{max}$ and $G_{min}$, which scales and offsets the general filter function. This scaling and offset modification is implemented using an enhancement filter function, $f_{ji}$. A plot of function $f_{ji}$ 822 with respect to filter number, "i", is illustrated in FIG. 8A so that its comparison to the general filter function $h_{ij}$ 820 can be seen. At 1014, the enhancement filter function, $f_{ji}$, is modified to take into account the edge effect. This edge effect modification is implemented using an edge effect filter function, $c_{ji}$. Since a finite number of filters are implemented on left and right sides of the filter, "j", there may be imbalance between the two sides. To compensate for the imbalance, an integral of the right side and the left side is calculated and if one side is larger than the other side, the smaller side is made bigger. At 1016, the contributions of the general filter function, $h_{ji}$, the enhancement filter function, $f_{ji}$, and edge effect filter function, $c_{ji}$, are combined to generate the scaling function, $W_{ji}$, which represents the scaling factor for each filter i, given filter j for which the enhancement is being calculated. The output of this scaling factor is the sum of the value for filter j added with the values of all other filters. The scaling factor generated for each filter is used to adjust the "lateral suppression" coefficients of the outer hair cell model.

In some implementations, the techniques may be used to adjust an MP3 sound processing strategy. Two masking effects are implemented in the MP3 strategy to eliminate sounds that cannot be perceived by the human ear. A simultaneous masking effect or "auditory masking" is dependent on the relationship between frequencies and their relative loudness. If a sound is close in frequency to a second sound, it is difficult for the human ear to distinguish the two sounds. Thus the simultaneous masking effect masks the sound with less information (lower frequency). In addition, simultaneous masking is dependent on time delay between two sounds. If a loud sound and a quiet sound are played simultaneously, the human ear cannot hear the quiet sound. However, if the same two sounds are played with a significant time delay in-between, the human hear is able to hear both sounds. Thus, temporal masking determines the length of time between the two sounds at which the second sound becomes audible. The length of time is set as a threshold for masking the quieter sound.

Figure 11:
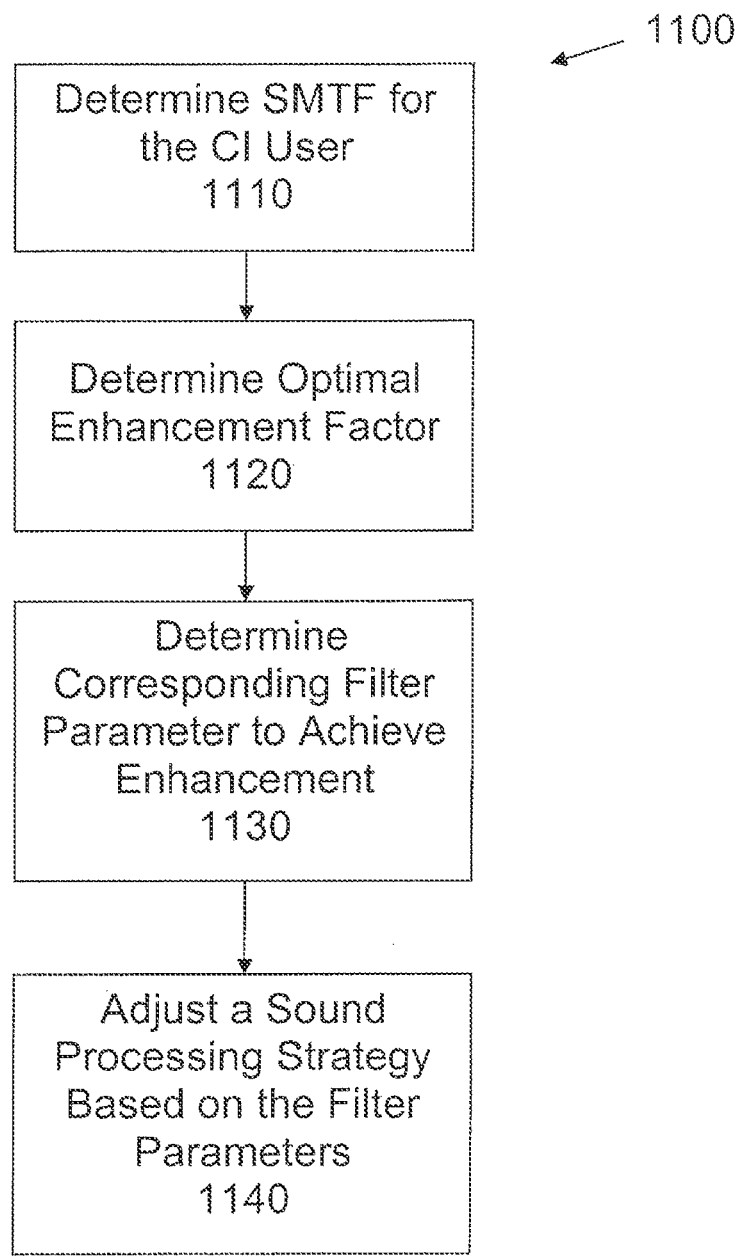
FIG. 11 is a flow chart of an exemplary spectral contrast enhancing process.

FIG. 11 is a process flow diagram that describes a general process of optimizing a spectral contrast enhancement strategy 1100 customized for the individual CI user. At 1110, a spectral modulation transfer function of a cochlear implant user is determined. At 1120, an enhancement factor for the determined spectral modulation transfer function is determined. At 1130, filter parameters are generated based on the spectral modulation transfer function and the enhancement factor. At 1140, a speech processing strategy is adjusted based on the generated filter parameters.

Figure 12:
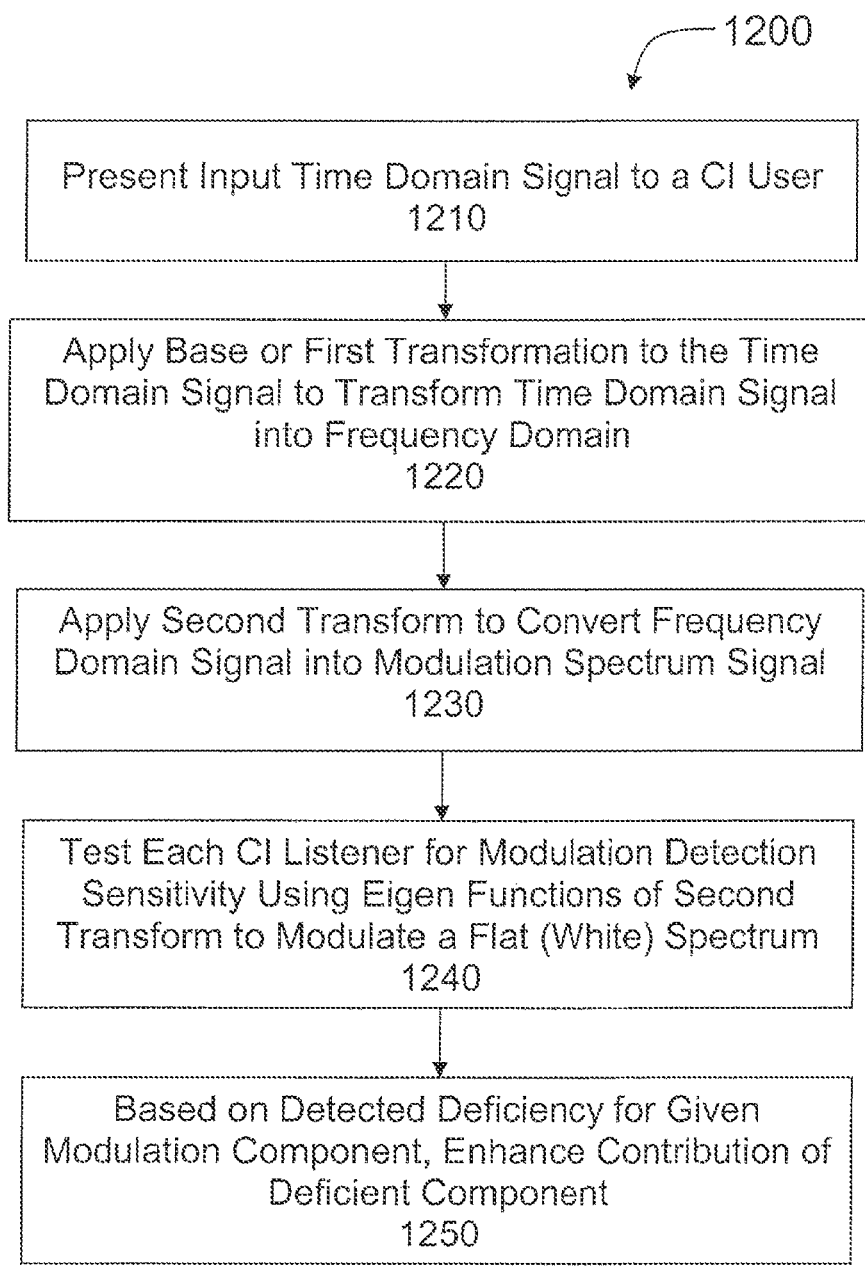
FIG. 12 is a process flow diagram illustrating another process of providing selective spectral contrast enhancement.

FIG. 12 is a process flow diagram illustrating another process 1200 of providing selective spectral contrast enhancement. As described above, speech coding strategies for Cochlear Implants represent the spectral shape of incoming sound on the CI listener's electrode array. Cochlear implant listeners rely upon the salience of this spectral representation to comprehend speech. Poor spatial selectivity of CI electrode arrays typically results in channel interactions that ultimately smears (or smoothes) the spectral representation that is ultimately available to the CI listener's central processing centers. Such undesired smearing can be overcome by improving the spectral contrast at the electrode array so that the perceptually relevant spectral features in the incoming sound are preserved. The amount by which the spectral contrast is increased is determined by measuring the degradation in modulation detection sensitivity for the individual CI listener.

The spectral representation of an input time domain signal can be characterized by expressing the input signal spectrum in terms of modulation frequency components. Decomposing the input signal spectrum into modulation frequency components can be accomplished by applying two transforms to the input signal spectrum. An input time domain signal s(t) representing a waveform during a sound frame is presented (1210) to a CI user. For example, the CI fitting portion 130 generates the signal s(t), and the sound processor portion 120 detects the generated signal s(t). A base or first transformation is applied (1220) to the time domain signal s(t) to transform the time domain signal into a frequency domain. The first transformation applied can include various linear transforms such as a Fast Fourier Transform (FFT), a wavelet transform, etc. (For more information regarding wavelet transformations, see http://en.wikipedia.org/wiki/Wavelet, which is submitted in the Information Disclosure Statement filed herewith, and which is incorporated herein by reference). herewith For example, using FFT, the first transform S(jω) can be expressed as shown in Equation (9):

$$S(j\omega) = FFT(s(t)) \tag{Eq. 9}$$

The first transform S(jω) can also involve a log-transformation that represents the obtained frequency domain signal as a log-magnitude spectrum. A corresponding log-magnitude spectrum of S(jω) is expressed as shown in Equation (10):

$$S(j\omega) = \log(FFT(s(t))) \tag{Eq. 10}$$

A second transform is applied (1230) to the first transform S(jω) to convert S(jω) into a modulation spectrum M(q). The modulation spectrum M(q) can be expressed as shown in Equation (11):

$$M(q) = FFT[S(j\omega)] = \sum_{k=1}^{N} m_k(q_k) \tag{Eq. 11}$$

The second transform can be used to express the frequency domain signal S(jω) as a sum of modulation components. For example, taking a second transform (e.g., a Fourier transform or a discrete-cosine-transform) of short term magnitude spectrum features generates the modulation spectrum, where the modulation spectrum is described by a sum of modulation components in q (i.e., cycles/Hz). In contrast to representing the signal spectrum in cycles/octave (CPO), by representing the spectrum in cycles/Hz, the input signal spectrum can be decomposed into discrete modulation components (in frequency). Since this technique uses uniform frequency decomposition, the resulting modulation frequency resolution is constant. In some implementations, an alternative transform such as the wavelet transform can be used as the second transform to yield a multi-scale modulation decomposition with a lower dimensionality compared to a linear frequency modulation spectrum.

Each CI listener can be tested for his/her modulation detection sensitivity for each of the modulation components. For example, each CI listener is tested (1240) for his/her modulation detection sensitivity using the Eigen functions of the second transform to modulate a flat (white) spectrum. For example, when the second transform applied is a Fourier transform, the Eigen functions of the second transform are pure sinusoids expressed in units of cycles/Hz. The sensitivity of each CI listener may be determined by measuring a psychometric function or by measuring his/her sensitivity to modulation at a fixed, pre-determined, modulation depth. This provides information regarding deficiencies for each of the modulation components. Any deficiency of each CI listener in his/her modulation detection sensitivity is expressed relative to the sensitivity of an average normal hearing listener.

Based on the detected deficiency for a given modulation component, the contribution of that deficient component is enhanced (1250) during signal reconstruction. Thus, the modulation spectrum can be selectively enhanced to provide the appropriate (i.e., customized) spectral contrast enhancement for each CI listener to overcome his/her deficiencies in spectral resolution as shown in Equation 12:

$$M_E(q) = \sum_{k=1}^{N} a_k \times m_k(q_k) \tag{Eq. 12}$$

where $a_k$ represents the enhancement coefficient corresponding to each $k_{th}$ modulation component.

An example implementation of the second transform can convert the log-magnitude spectrum into a Fourier series having the form as shown in Equation (13):

$$M(q) = \sum_{k=1}^{N} a_k \cos(q_k) \text{ or } M(q) = \sum_{k=1}^{N} a_k e^{iq_k} \quad \text{(Eq. 13)}$$

The modulation components in such an expansion are sinusoids in linear frequency (cycles/Hz) and spectral contrast can be enhanced by selectively amplifying the enhancement coefficients $a_k$.

Figure 13:
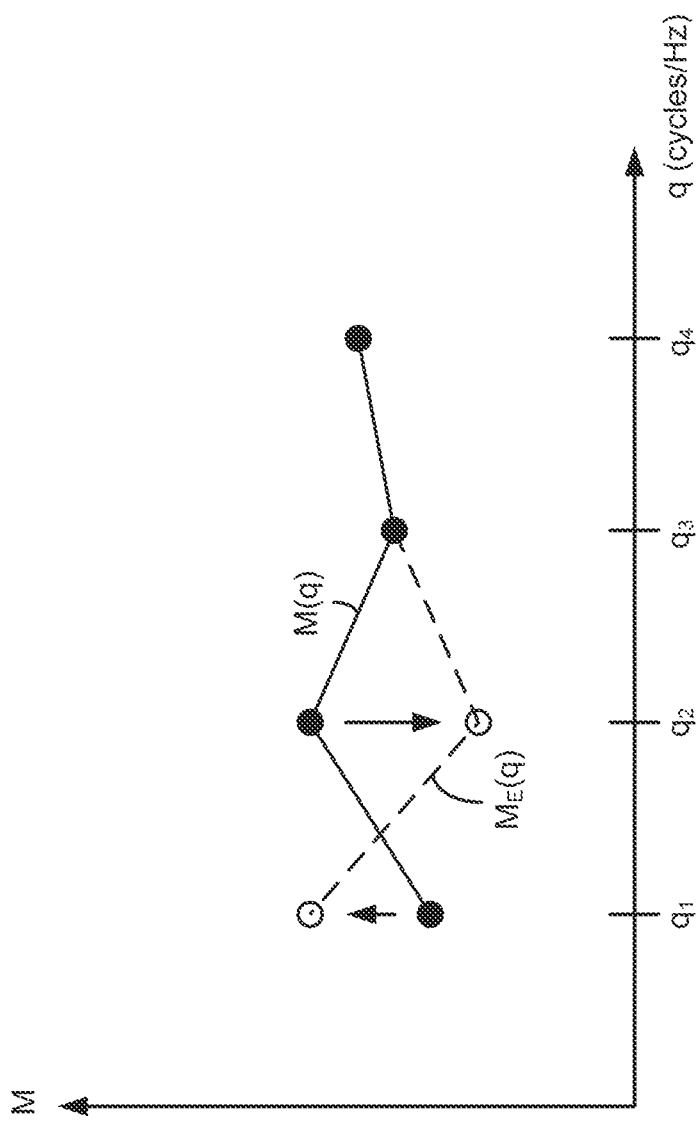
FIG. 13 shows modification of a modulation spectrum.

The modulation spectrum, M(q), need not strictly comprise a summation of components, but rather can simply comprise any function of q, such as is illustrated in FIG. 13. In such a case, enhancement may occur through any modification of the modulation spectrum. In other words, enhancement need not merely be achieved by adjustment of the enhancement coefficients of the summed modulation series of Equation 13. For example, FIG. 13 illustrates a generalized modulation spectrum M(q) represented by black dots $q_1$ through $q_4$. As shown, the first two q values have been changed: $q_1$ has been increased and $q_2$ has been decreased to arrive at an enhanced modulation spectrum, $M_E(q)$. The extent to which modulation values q are change will depend on a given user's modulation sensitivities.

Once the modulation spectrum has been varied in the sound processor 126 (FIG. 1) to enhance spectral contrast using the techniques just discussed, the sound processor 26 then takes the inverse transform of the modulation spectrum to return to the frequency domain, $S_E(j\omega)$.

$$S_E(j\omega) = \text{IFFT}[M_E(q)] \quad \text{(Eq. 14)}$$

After being converted to the frequency domain, the data is essentially in the form of envelope signals $E_1$-$E_k$ (FIG. 5) and is ready for acoustic to electrical mapping, and for broadcast to the cochlear implant 150.

Figure 14A:
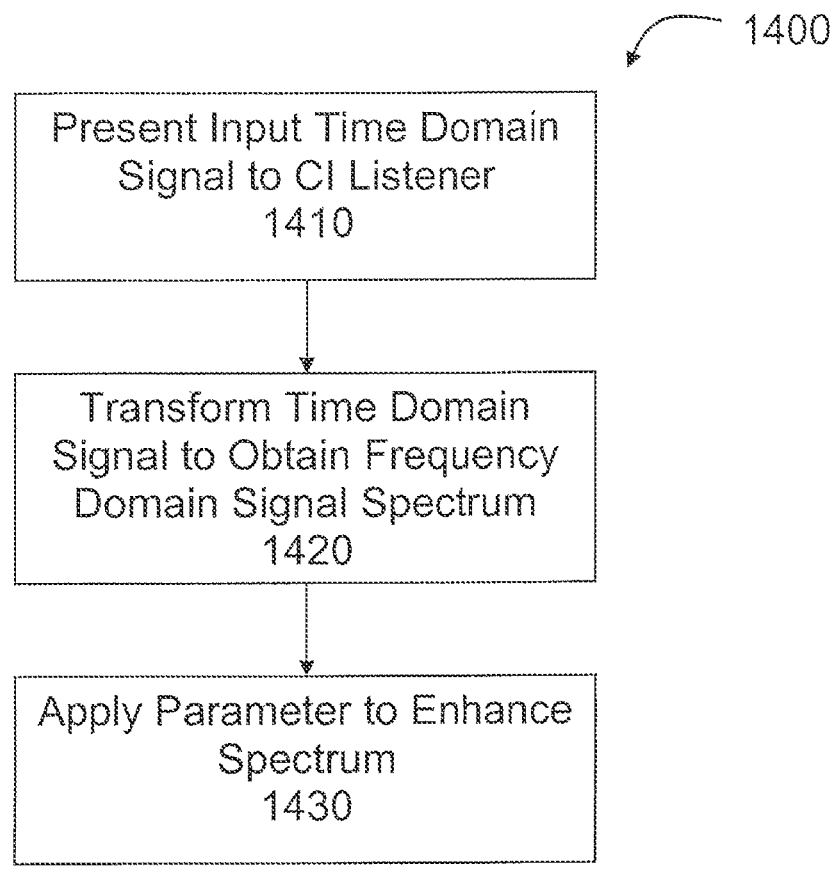
FIGS. 14A and B are process flow diagrams showing a process of providing frequency dependent spectral contrast enhancement.
Figure 14B:
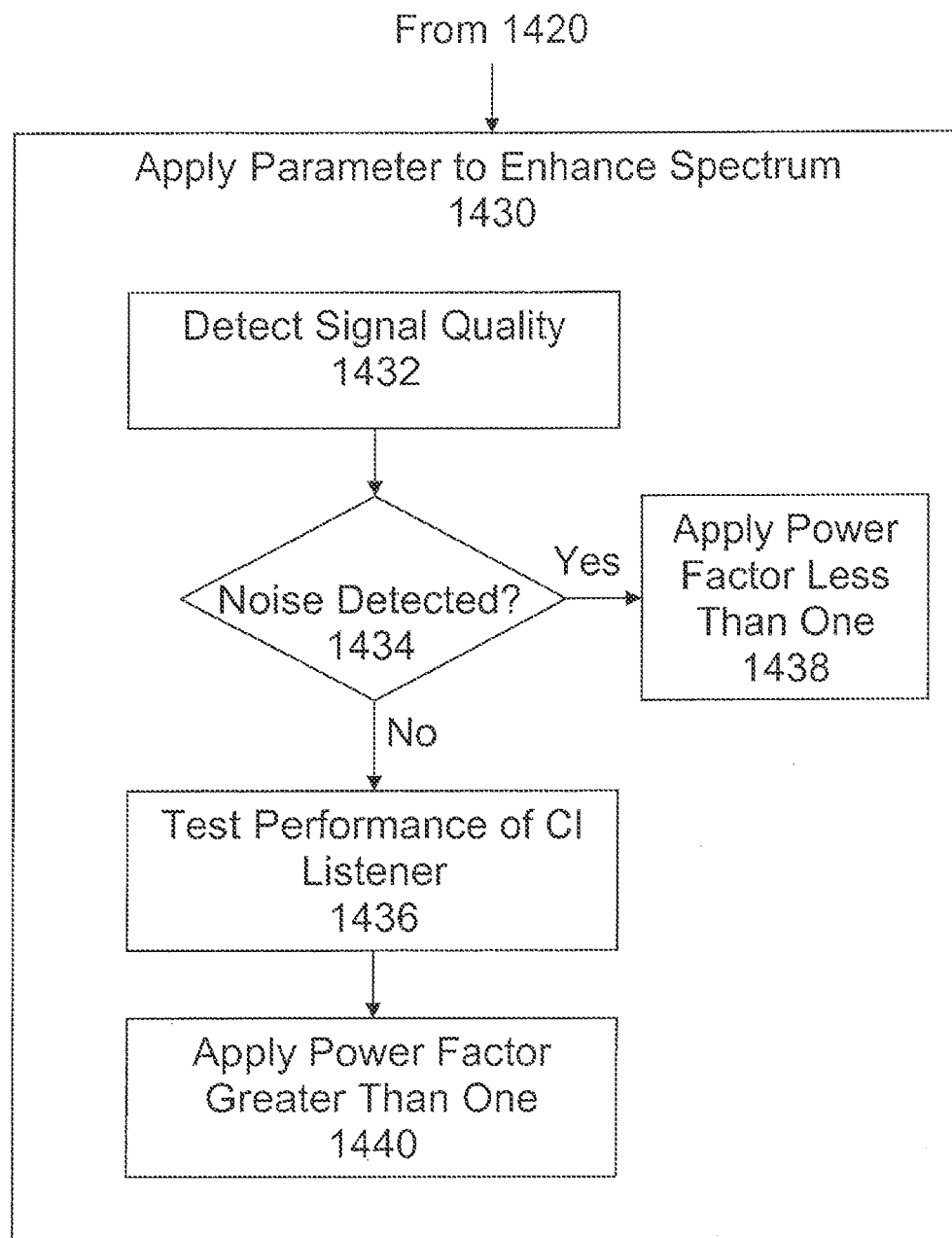

Another technique for enhancing spectral contrast in a frequency dependent manner is illustrated in FIGS. 14A and 14B. FIG. 14A is a process flow diagram illustrating a process 1400 of enhancing spectral contrast of input signal in a frequency dependent manner. The spectral contrast of the incoming sound spectrum can be selectively enhanced (or increased) by an amount that can be controlled by a simple parameter. Enhancement of the signal includes increasing the signal peak-to-trough ratio. A sound frame in time domain, denoted by s(t) is presented (1410) to a CI listener. The time domain signal is transformed (1420) to obtain a corresponding signal spectrum, $S(j\omega)$ in frequency domain. An enhanced spectrum $S_E(j\omega)$ is determined (1430) by applying a power factor parameter $a(\omega)$ to the signal spectrum as shown in Equation (14):

$$S_E(j\omega) = S(j\omega)^{a(\omega)} \quad \text{(Eq. 15)}$$

where the power factor, $a(\omega)$ is a positive frequency dependent number. The power factor can be set by a clinician during the CI fitting. Alternatively, the CI listener may be able to adjust the power factor on his/her own. Since the power factor is a frequency dependent parameter, the spectral contrast can be enhanced in a frequency-dependent manner. To enhance the spectrum, a positive, frequency dependent number greater than one is selected. The magnitude of the selected power factor may vary based on various factors, e.g., the distinctive sensitivity of each CI listener to detect spectral contrasts and any detection of noise. Various CI listeners may require varying degrees of enhancements that are different from each other.

FIG. 14B shows in more detail a process 1430 used to apply the power factor $a(\omega)$ to enhance the frequency spectrum. As described above, the signal quality is detected (1432). When detected (1434) that noise is present in the signal at the frequency under test, a power factor that is less than one is applied (1438) to suppress the noise. When noise is not detected, performance of each CI listener can be implemented (1436). An appropriate enhancement factor that is larger than one is applied (1440) to enhance the signal in frequency dependent manner. Thus, in this illustration, the frequency dependent enhancement is adapted or applied selectively based on the detected signal quality, such that detected noise (e.g., background noise during conversation) is selectively not enhanced.

Figure 15:
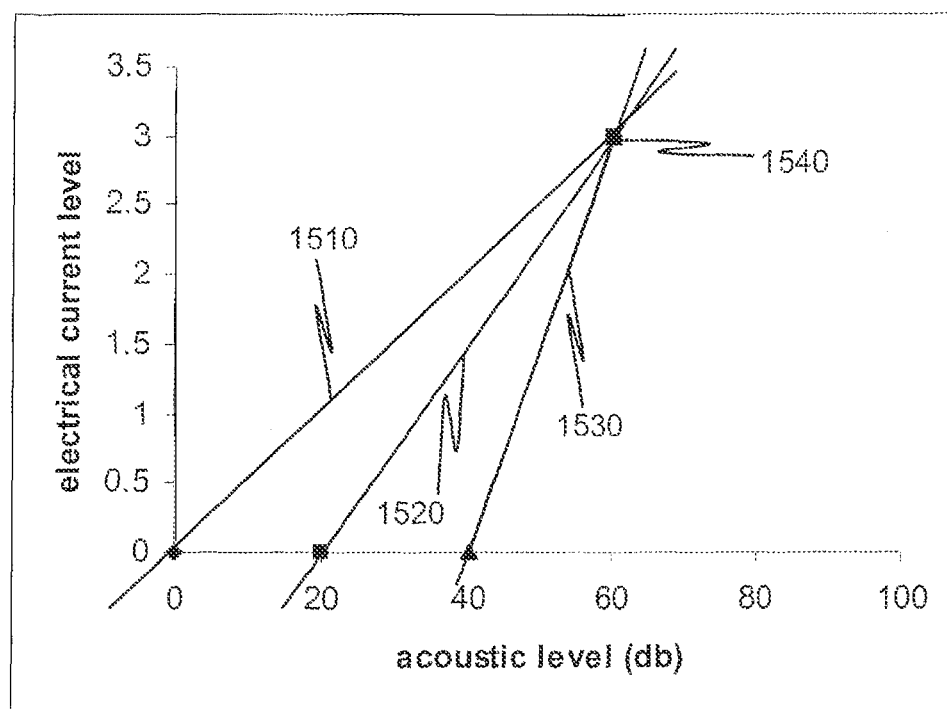
FIG. 15 is a chart illustrating electrical-to-acoustical mappings.

The enhancement factor, $a(\omega)$ (or other variations) can be used to adjust the width of the instantaneous dynamic range (IDR) of each CI listener. The IDR is the range between the maximum comfort level and the threshold level. FIG. 15 illustrates an electrical-to-acoustical mapping for a normal listener 1510 and CI listeners 1520 and 1530. The y-axis represents the electrical current level (units not shown for illustrative purposes) and the x-axis represents the sound level in decibel (db). For a normal listener 1510, the maximum comfort level 1540 is mapped as 60 db and about 3 units of current, and the sound threshold level 1550 is mapped as 0 db and a very small current. For the CI listeners 1520 and 1530, the maximum comfort level 1540 is maintained at the 60 db point since the comfort sound level should not change (i.e., don't want too loud of a sound). However, the threshold level may be mapped at a higher sound level (e.g., due to a level of noise). For the exemplary CI listeners, 1520 and 1530, the threshold levels has changed to 20 db and 40 db respectively. Thus, the 20 db and 40 db levels are mapped to zero current. The adjusted threshold level is desirable since the CI listeners 1520 and 1530 are not able to effectively detect (i.e., hear) below the adjusted threshold levels. The levels mapped for individual CI listeners may be determined by noise estimation. For example, for the CI listeners 1520 and 1530, levels below the 20 db and 40 db levels may be contaminated by noise.

As shown in FIG. 15, Equation 15 and variations thereof can be applied to mathematically decrease the IDR customized for each CI listener. For example, the IDR has been decreased to 40 db and 20 db for exemplary CI listeners 1520 and 1530 respectively. The IDR for each CI listener can be measured using psychophysical measurement as described above. The tradeoff for each CI listener is between having a wide IDR (desirable to obtain lots of sound) and having good discriminability of different sound level. While having a wide IDR is desirable to detect lots of sound, CI listeners may not be able to detect some of the lower sound levels due to noise. Thus, the lower sound levels are sacrificed (i.e., filtered out) by increase the slope of the lines that pass through the comfort point (60 db) and the threshold point (zero electrical point). IDR can be adjusted based on a fixed IDR factor (performance of each CI listener) and a dynamic factor (detected noise estimate at each frequency channel.)

Figure 16:
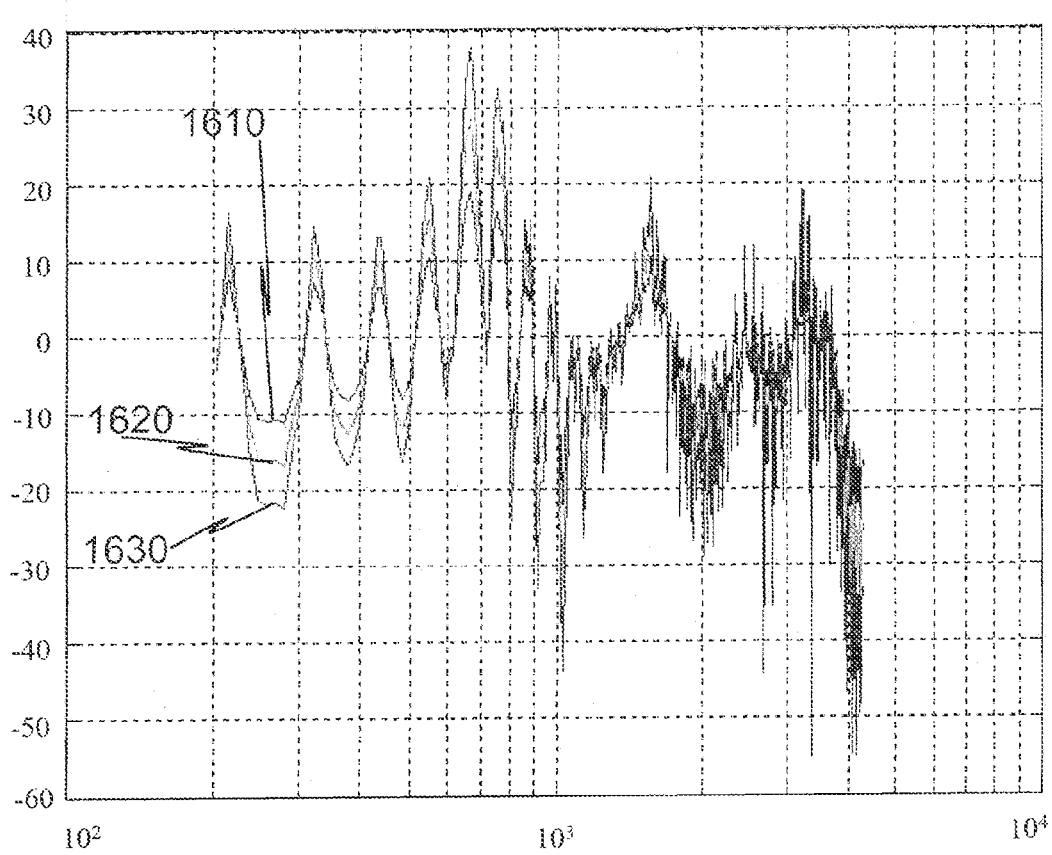
FIG. 16 is a chart illustrating exemplary effects of applying positive, frequency dependent enhancement parameters.

FIG. 16 shows an exemplary data representation of the spectral enhancement that can be achieved using the Equation 15. The y-axis represents the acoustic level (e.g., db) and the x-axis represents log of the frequency. In this example, the original spectrum curve 1610 is shown with contrast enhancement curves 1620 and 1630 set to $a(\omega)=1.5$ and 2 respectively for all frequencies.

In some implementations, the root-mean-square (RMS) or the net energy in the input signal can be dynamically tracked. And based on the tracked RMS level of the signal, the overall gain of an enhanced signal can be presented for each CI listener. The overall gain is dynamically selected to match the RMS of the input signal.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a propagated signal or a computer readable medium. The propagated signal is an artificially generated signal, e.g., a machine-generated electrical, optical, or electromagnetic signal, that is generated to encode information for transmission to suitable receiver apparatus for execution by a computer. The computer readable medium can be a machine-readable storage device, a machine-readable storage substrate, a memory device, a composition of matter effecting a machine-readable propagated signal, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, input from the user can be received in any form, including acoustic, speech, or tactile input.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

What is claimed is:

1. A method for enhancing the operation of a cochlear implant system, comprising:
   receiving a time domain signal at sound processing circuitry of a user;
   applying at the sound processing circuitry a transformation to the time domain signal to form an initial frequency domain signal; and
   applying at the sound processing circuitry an exponent to the initial frequency domain signal to produce an enhanced frequency domain signal, wherein the enhanced frequency domain signal has an increased contrast when compared to the initial frequency domain signal.

2. The method of claim 1, wherein the exponent is frequency dependent.

3. The method of claim 1, further comprising detecting a signal quality of the initial frequency domain signal at each frequency.

4. The method of claim 3, wherein applying the exponent comprises applying the exponent at each frequency in the initial frequency domain signal with acceptable signal quality.

5. The method of claim 4, wherein applying the exponent comprises suppressing each frequency with unacceptable signal quality in the enhanced frequency domain signal.

6. The method of claim 1, wherein the sound processing circuitry is contained within an external component of the cochlear implant system.

7. The method of claim 1, further comprising transmitting the enhanced frequency domain signal to the cochlear implant of a user.

8. The method of claim 7, wherein the wherein the exponent is greater than one at each frequency with acceptable signal quality.

9. The method of claim 8, wherein the exponent is less than one at each frequency with unacceptable signal quality.

* * * * *